US006232458B1

(12) United States Patent
Weiss et al.

(10) Patent No.: US 6,232,458 B1
(45) Date of Patent: *May 15, 2001

(54) SYNTHETIC POLYNUCLEOTIDES ENCODING TROPOELASTIN

(75) Inventors: Anthony Steven Weiss, Sydney (AU); Stephen Lewis Martin, Sedgley (GB)

(73) Assignee: The University of Sydney, Sydney (AU)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/464,700

(22) PCT Filed: Dec. 16, 1993

(86) PCT No.: PCT/AU93/00655

§ 371 Date: Jul. 24, 1995

§ 102(e) Date: Jul. 24, 1995

(87) PCT Pub. No.: WO94/14958

PCT Pub. Date: Jul. 7, 1994

(30) Foreign Application Priority Data

Dec. 22, 1992 (AU) .................................................. PL 6520
Jun. 28, 1993 (AU) .................................................. PL 9661

(51) Int. Cl.$^7$ .......................... C07H 21/04; A61K 38/39; C12N 1/21
(52) U.S. Cl. ....................... 536/23.5; 536/24.2; 536/24.1; 536/23.4; 435/320.1; 435/252.33; 435/254.1; 435/254.2; 435/69.1; 435/69.7; 530/353; 514/2; 514/12
(58) Field of Search .................................. 536/23.5, 24.2, 536/24.1, 23.4; 435/320.1, 240.2, 240.4, 252.33, 254.1, 254.2, 69.1, 69.7; 530/353; 514/2, 12

(56) References Cited

U.S. PATENT DOCUMENTS

| | | | |
|---|---|---|---|
| 4,474,851 | 10/1984 | Urry | 428/373 |
| 4,783,523 | 11/1988 | Urry | 530/323 |
| 4,952,496 | 8/1990 | Studier | 435/91 |
| 5,250,516 | 10/1993 | Urry | 514/17 |

OTHER PUBLICATIONS

Y. Gursky et al, "The Increase in Gene Expression Induced by Introduction of Rare Codons into the C Terminus of the Template", *Gene*, 148: 15–21 (1994).
P. Stopien et al, "Synthesis of a Human Insulin Gene, VI. Expression of the Synthetic Proinsulin Gene in Yeast", *Gene*, 24:289–297 (1983).
S. Makrides, "Strategies for Achieving High–Level Expression of Genes in *Escherichia coli*", *Microbiological Reviews*, 60(3):512–538 (Sep., 1996).

M. Tassabehji et al, "Elastin: Genomic Structure and Point Mutations in Patients with Supravalvular Aortic Stenosis", *Human Molecular Genetics*, 6(7):1029–1036 (1997).
S. Martin et al, "Total Synthesis andExpression in *Escherichia coli* of a Gene Encoding Human Tropoelastin", *Gene*, 154:159–166 (1995).
W. Parks et al, "Tropoelastin heterogeneity: Implications for Protein Function and Disease", *Am. J. Respir. Cell Mol. Biol.*, 2:399–406 (1990).
J. Janne et al, "Transgenic Animals as Bioproducers of Therapeutic Proteins", *Annals of Medicine*, 24(4):273–280 (Aug. 1992) (Abstract Only).
L. Isola et al, "Transgenic Animals: A New Era in Developmental Biology and Medicine", *Biotechnology*, 16:3–20 (1991) (Abstract Only).
L. Frohman et al, "Regulation of Growth Hormone–Releasing Hormone Gene Expression and Biosynthesis", *Yale Journal of Biology & Medicine*, 62(5):427–433 (Sep.–Oct., 1989) (Abstract Only).
A. Clark et al, "The Molecular Manipulation of Milk Composition", *Genome*, 31(2):950–955 (1989) (Abstract Only).
U. Storb et al, "Expression of Immunoglobulin Genes in Transgenic Mice and Transfected Cells", *Annals of the New York Academy of Sciences*, 546:51–56 (1988) (Abstract Only).
M. Holzenberger et al, "Quantitation of Tropoelastin mRNA and Assessment of Alternative Splicing in Human Skin Fibroblasts by Reverse Transcriptase–Polymerase Chain Reaction", *PCR Methods & Applications*, 3(2):107–114 (Oct., 1993) (Abstract Only).
J. Rosenbloom et al, "Structure of the Elastin Gene", *Ciba Foundation Symposium*, 192:59–80 (1995).
Novagen Product Brochure, "pET Expression Systems", pp. 47 and 1–3 (Feb. 2, 1998).
B. Lewin, Genes VI, Chapter 9, pp. 214–215, Oxford Press Inc., New York (1997).
J. Rosenbloom et al, "Elastin Genes and Regulation of Their Expression", *Critical Reviews in Eukaryotic Gene Expression*, CRC Press Inc., vol. 1, No. 3, pp. 145–156 (1990) [Rosenbloom I].
Z. Indik et al, "Production of Recombinant Human Tropoelastin: Characterization and Demonstration of Immunologic and Chemotactic Activity", *Arch. Biochem. Biophys.*, 280(1):80–86 (Jul., 1990) [Indik I].
G. Bressan et al, "Repeating Structure of Chick Tropoelastin Revealed by Complementary DNA Cloning", *Biochemistry*, 26(6):1497–1503 (Mar. 24, 1987).

(List continued on next page.)

*Primary Examiner*—David Romeo
(74) *Attorney, Agent, or Firm*—Howson and Howson

(57) ABSTRACT

Recombinant tropoelastins and variants of recombinant tropoelastins produced from synthetic polynucleotides, as well as the synthetic polynucleotides themselves are provided. Also provided are cross-linked elastins or elastin-like products prepared from the tropoelastins or variants.

24 Claims, 21 Drawing Sheets

OTHER PUBLICATIONS

J. Cappello et al, "Genetic Engineering of Structural Protein Polymers", *Biotechnol. Prog.*, 6:198–202 (May/Jun., 1990).

J. Rosenbloom et al, "Regulation of Elastin Gene Expression", *Ann. New York Acad. Sci.*, 624:116–136 (1991) [Rosenbloom II].

D. McPherson et al, "Production and Purification of a Recombinant Elastomeric Polypeptide, G–(VPGVG)19–VPGV, from *Escherichia coli*", *Biotechnol. Prog.*, 8:347–352 (Jul./Aug., 1992).

V–M. Kahari et al, "Deletion Analyses of 5'–Flanking Region of the Human Elastin Gene, Delineation of Functional Promoter and Regulatory cis–Elements", *J. Biol. Chem.*, 265(16):9485–9490 (Jun. 5, 1990).

K. Raju et al, "Primary Structures of Bovine Elastin a, b, and c Deduced from the Sequences of cDNA Clones", *J. Biol. Chem.*, 262(12):5755–5762 (Apr. 25, 1987).

M. Fazio et al, "Cloning of Full–length Elastin cDNAs from a Human Skin Fibroblast Recombinant cDNA Library: Further Elucidation of Alternative Splicing Utilizing Exon–specific Oligonucleotides", *J. Invest. Dermatol.*, 91(5):458–464 (Nov., 1988).

Z. Indik et al, "Alternative Splicing of Human Elastin mRNA Indicated by Sequence Analysis of Cloned Genomic and Complementary DNA", *Proc. Natl. Acad. Sci. USA*, 84:5680–5684 (Aug., 1987) [Indik II].

L. Olliver et al, "The Gene Coding for Tropoelastin is Represented as a Single Copy Sequence in the Haploid Sheep Genome", *Collagen Rel. Res.*, 7:77–89 (1987).

M. Alting–Mees et al, "pBluescript II: Gene Mapping Vectors", *Nucl. Acids Res.*, 17(22):9494 (1989).

J. Gough et al, "Sequence Diversity Among Related Genes for Recognition of Specific Targets in DNA Molecules", *J. Mol. Biol.*, 166:1–19 (May 5, 1983).

J. Short et al, "lambda ZAP; a Bacteriophage lambda Expression Vector with in vivo Excision Properties", *Nucl. Acids Res.*, 16(15):7583–7600 (1988).

D. Smith et al, "Single–step Purification of Polypeptides Expressed in *Escherichia coli* as Fusions with Glutathione S–transferase", *Gene*, 67:31–40 (1988).

F. Studier et al, "Use of T7 RNA Polymerase to Direct Expression of Cloned Genes", *Meth. Enzymol.*, 185:77–89 (May, 1990).

R. Heim et al, "Alternative Splicing of Rat Tropoelastin mRNA is Tissue–Specific and Developmentally Regulated", *Matrix*, 11:359–366 (1991).

H. Yeh et al, "Sequence Variation of Bovine Elastin mRNA Due to Alternative Splicing", *Collagen Rel. Res.*, 7:235–247 (1987).

S. Zhang et al, "Low–usage Codons in *Escherichia coli*, Yeast, Fruit Fly and Primates", *Gene*, 105:61–72 (1991).

C. Newgard et al, "Sequence Analysis of the cDNA Encoding Human Liver Glycogen Phosphorylase Reveals Tissue–Specific Codon Usage", *Proc. Natl. Acad. Sci. USA*, 83:8132–8136 (Nov., 1986).

E. Murray et al, "Codon Usage in Plant Genes", *Nucl. Acids Res.*, 17(2):477–498 (1989).

D. Urry et al, "Temperature Dependence of Length of Elastin and its Polypentapeptide", *Biochem. Biophys. Res. Comm.*, 141(2):749–755 (Dec. 15, 1986).

D. Bedell–Hogan et al, "Oxidation, Cross–linking, and Insolubilization of Recombinant Tropoelastin by Purified Lysyl Oxidase", *J. Biol. Chem.*, 268(14):10345–10350 (May 15, 1993).

L. Sandberg et al, "Tropoelastin Purification from Copper–Deficient Swine: A Simplified Method", *Biochim. Biophys. Acta.*, 236:542–545 (1971).

W. Bullock et al, "XL1–Blue: A High Efficiency Plasmid Transforming recA *Escherichia coli* Strain with Beta–Galactosidase Selection", *BioTechniques*, 5(4):376–378 (May/Jun., 1987).

D. Lipman et al, "Rapid and Sensitive Protein Similarity Searches", *Science*, 227:1435–1441 (Mar. 22, 1985).

S. Yoshifuji et al, "Chemical Conversion of L–alpha, omega– Diamino Acids to L–omega–Carbamoyl–alpha–amino Acids by Ruthenium Tetroxide Oxidation", *Chem. Pharm. Bull.*, 35(7):2994–3001 (1987).

R. Rapaka et al, "Synthesis of Polypeptide Models of Elastin, Synthesis and Properties of a Cross–Linked Polytetrapeptide", *Int. J. Peptide Protein Res.*, 21:352–363 (1983).

Sharp et al. The codon Adaptation Index—a measure of directional synonymous codon usage bias, and its potential applications. Nucleic Acids Research, (Feb. 11, 1987) 15 (3) 1281–95.*

Sharp et al. Codon usage in regulatory genes in *Escherichia coli* does not reflect selection for 'rare' codons. Nucleic Acids Research, (Oct. 10, 1986) 14 (19) 7737–49.*

Khorana H. G. Total synthesis of a gene. Science, Feb. 16, 1979, 203;614–625.*

Mathur et al. Analysis of codon usage in genes for nitrogen–fixation from Phylogenetically diverse diazotrophs. J. Mol. Evol., (May 1991) vol. 32, No. 5, pp. 364–373.*

Williams et al. Design, synthesis and expression of a human interleukin–2 gene incorporating the codon usage bias found in highly expressed *Escherichia–coli* genes. Nucleic Acids Research, (1988) vol. 16, No. 22, pp. 10453–10467.*

Chavancy et al. Effect of tRNA pool balance on rate and uniformity of elongation during translation of fibroin mRNA in a reticulocyte cell–free system. Biochimie, (Jul. 1981) 63 (7) 611–8.*

Kalman et al. Synthesis of a gene for human serum albumin and its expression in *Saccharomyces cerevisiae*. Nuc. Acids Res. 18: 6075–6081 (1990).*

Simoncsits et al. Synthesis, cloning and expression in *Escherichia coli* of artificial genes coding for biologically active elongated precursors of the vasoactive intestinal polypeptide. Eur. J. Biochem. (1988), 178(2), 343–50.*

Cserpan et al. Conversion of single–stranded oligonucleotides into cloned duplexes and its consecutive application to short artificial genes. Acta Chem. Scand. (1991), 45(3), 265–72.*

Wosnick et al. Gene, 60 (1987) 115–127.*

Itakura et al. Science, 198 (1977) 1056–1063.*

Sandberg et al. Production and isolation of soluble elastin from copper–deficient swine. Methods Enzymol 82:657–665 (1982).*

Bowie J U; Reidharr–Olson J F; Lim W A; Sauer R T. Deciphering the message in protein sequences: tolerance to amino acid substitutions. Science, (Mar. 16, 1990) 247 (4948) 1306–10.*

Alberts et al., Molecular Biology of the Cell, 1994, Garland Publishing, Inc., New York, NY, pp. 115–116.*

Sambrook et al. Molecular Cloning: A Laboratory Manual Second Edition vols. 1, 2 and 3. Cold Spring Harbor Laboratory Press: Cold Spring Harbor, New York, U.S.A. Nov., 1989.*

George et al, "Current methods in sequence comparison and analysis, " in Macromolecular Sequencing and Synthesis, Selected Methods and Applications, 1988, D.H.Schlesinger (ed.), Alan R. Liss, Inc., New York, NY, pp. 127–149.*

Barton, "Protein sequence alignment and database scanning, " in Protein Structure Prediction, A Practical Approach, 1996 IRL Press at Oxford University Press, Oxford, UK, pp. 31–63.*

Makoff et al. Expression of tetanus toxin fragment C in *E. coli*: high level expression by removing rare codons. Nucleic Acids Res 17: 10191–10202 (1989).*

* cited by examiner

```
  1  GATCCATGGGTGGCGTTCCGGGTGCTATCCCGGGTGGCGTTCCGGGTGGTGTATTCTACC    60
     GTACCCACCGCAAGGCCCACGATAGGGCCCACCGCAAGGCCCACCACATAAGATGG
      S  M  G  G  V  P  G  A  I  P  G  G  V  P  G  G  V  F  Y  P

61  CAGGCGCGGGTCTGGGTGCACTGGGCGGTGGTGCGCTGGGCCCGGGTGGTAAACCGCTGA   120
     GTCCGCGCCCAGACCCACGTGACCCGCCACCACGCGACCCGGGCCCACCATTTGGCGACT
      G  A  G  L  G  A  L  G  G  A  L  G  P  G  G  K  P  L  K

121  AACCGGTTCCAGGCGGTCTGGCAGGTGCTGGTCTGGGTGCAGGTCTGGGCGCGTTCCCGG   180
     TTGGCCAAGGTCCGCCAGACCGTCCACGACCAGACCCACGTCCAGACCCGCGCAAGGGCC
      P  V  P  G  G  L  A  G  A  G  L  G  A  G  L  G  A  F  P  A

181  CGGTTACCTTCCCGGGTGCTCTGGTTCCGGGTGGCGTTGCAGACGCAGCTGCTGCGTACA   240
     GCCAATGGAAGGGCCCACGAGACCAAGGCCCACCGCAACGTCTGCGTCGACGACGCATGT
      V  T  F  P  G  A  L  V  P  G  G  V  A  D  A  A  A  A  Y  K

241  AAGCGGCAAAGGCAGGTGCGGGTCTGGGCGGGGTACCAGGTGTTGGCGGTCTGGGTGTAT   300
     TTCGCCGTTTCCGTCCACGCCCAGACCCGCCCCATGGTCCACAACCGCCAGACCCACATA
      A  A  K  A  G  A  G  L  G  G  V  P  G  V  G  G  L  G  V  S

301  CTGCTGGCGCAGTTGTTCCGCAGCCGGGTGCAGGTGTAAAACCGGGCAAAGTTCCAGGTG   360
     GACGACCGCGTCAACAAGGCGTCGGCCCACGTCCACATTTTGGCCCGTTTCAAGGTCCAC
      A  G  A  V  V  P  Q  P  G  A  G  V  K  P  G  K  V  P  G  V

361  TTGGTCTGCCGGGCGTATACCCGGGTGGTGTTCTGCCGGGCGCGCGTTTCCCAGGTGTTG   420
     AACCAGACGGCCCGCATATGGGCCCACCACAAGACGGCCCGCGCGCAAAGGGTCCACAAC
      G  L  P  G  V  Y  P  G  G  V  L  P  G  A  R  F  P  G  V  G
```

FIG. 3(a)

```
421  GTGTACTGCCGGGCGTTCCGACCGGTGCAGGTGTTAAACCGAAGGCACCAGGTGTAGGCG   480
     CACATGACGGCCCGCAAGGCTGGCCACGTCCACAATTTGGCTTCCGTGGTCCACATCCGC

V  L  P  G  V  P  T  G  A  G  V  K  P  K  A  P  G  V  G  G

481  GCGCGTTCGCGGGTATCCCGGGTGTTGGCCCGTTCGGTGGTCCGCAGCCAGGCGTTCCGC   540
     CGCGCAAGCGCCCATAGGGCCCACAACCGGGCAAGCCACCAGGCGTCGGTCCGCAAGGCG

A  F  A  G  I  P  G  V  G  P  F  G  G  P  Q  P  G  V  P  L

541  TGGGTTACCCGATCAAAGCGCCGAAGCTTCCAGGTGGCTACGGTCTGCCGTACACCACCG   600
     ACCCAATGGGCTAGTTTCGCGGCTTCGAAGGTCCACCGATGCCAGACGGCATGTGGTGGC

G  Y  P  I  K  A  P  K  L  P  G  G  Y  G  L  P  Y  T  T  G

601  GTAAACTGCCGTACGGCTACGGTCCGGGTGGCGTAGCAGGTGCTGCGGGTAAAGCAGGCT   660
     CATTTGACGGCATGCCGATGCCAGGCCCACCGCATCGTCCACGACGCCCATTTCGTCCGA

K  L  P  Y  G  Y  G  P  G  G  V  A  G  A  A  G  K  A  G  Y

661  ACCCAACCGGTACTGGTGTTGGTCCGCAGGCTGCTGCGGCAGCTGCGGCGAAGGCAGCAG   720
     TGGGTTGGCCATGACCACAACCAGGCGTCCGACGACGCCGTCGACGCCGCTTCCGTCGTC

P  T  G  T  G  V  G  P  Q  A  A  A  A  A  A  K  A  A  A

721  CAAAATTCGGCGCGGGTGCAGCGGGTGTTCTGCCGGGCGTAGGTGGTGCTGGCGTTCCGG   780
     GTTTTAAGCCGCGCCCACGTCGCCCACAAGACGGCCCGCATCCACCACGACCGCAAGGCC

K  F  G  A  G  A  A  G  V  L  P  G  V  G  G  A  G  V  P  G

781  GTGTTCCAGGTGCGATCCCGGGCATCGGTGGTATCGCAGGCGTAGGTACTCCGGCGGCCG   840
     CACAAGGTCCACGCTAGGGCCCGTAGCCACCATAGCGTCCGCATCCATGAGGCCGCCGGC

V  P  G  A  I  P  G  I  G  G  I  A  G  V  G  T  P  A  A

841  CTGCGGCTGCGGCAGCTGCGGCGAAAGCAGCTAAATACGGTGCGGCAGCAGGCCTGGTTC   900
     GACGCCGACGCCGTCGACGCCGCTTTCGTCGATTTATGCCACGCCGTCGTCCGGACCAAG

```
901  CGGGTGGTCCAGGCTTCGGTCCGGGTGTTGTAGGCGTTCCGGGTGCTGGTGTTCCGGGCG   960
     GCCCACCAGGTCCGAAGCCAGGCCCACAACATCCGCAAGGCQCACGACCACAAGGCCCGC

G  G  P  G  F  G  P  G  V  V  G  V  P  G  A  G  V  P  G  V

961  TAGGTGTTCCAGGTGCGGGCATCCCGGTTGTACCGGGTGCAGGTATCCCGGGCGCTGCGG  1020
     ATCCACAAGGTCCACGCCCGTAGGGCCAACATGGCCCACGTCCATAGGGCCCGCGACGCC

G  V  P  G  A  G  I  P  V  V  P  G  A  G  I  P  G  A  A  V

1021 TTCCAGGTGTTGTATCCCCGGAAGCGGCAGCTAAGGCTGCTGCGAAAGCTGCGAAATACG  1080
     AAGGTCCACAACATAGGGGCCTTCGCCGTCGATTCCGACGACGCTTTCGACGCTTTATGC

P  G  V  V  S  P  E  A  A  A  K  A  A  A  K  A  A  K  Y  G

1081 GAGCTCGTCCGGGCGTTGGTGTTGGTGGCATCCCGACCTACGGTGTAGGTGCAGGCGGTT  1140
     CTCGAGCAGGCCCGCAACCACAACCACCGTAGGGCTGGATGCCACATCCACGTCCGCCAA

A  R  P  G  V  G  V  G  G  I  P  T  Y  G  V  A  G  G  F

1141 TCCCAGGTTTCGGCGTTGGTGTTGGTGGCATCCCGGGTGTAGCTGGTGTTCCGTCTGTTG  1200
     AGGGTCCAAAGCCGCAACCACAACCACCGTAGGGCCCACATCGACCACAAGGCAGACAAC

P  G  F  G  V  G  V  G  G  I  P  G  V  A  G  V  P  S  V  G

1201 GTGGCGTACCGGGTGTTGGTGGCGTTCCAGGTGTAGGTATCTCCCCGGAAGCGCAGGCAG  1260
     CACCGCATGGCCCACAACCACCGCAAGGTCCACATCCATAGAGGGGCCTTCGCGTCCGTC

G  V  P  G  V  G  G  V  P  G  V  G  I  S  P  E  A  Q  A  A

1261 CTGCGGCAGCTAAAGCAGCGAAGTACGGCGTTGGTACTCCGGCGGCAGCAGCTGCTAAAG  1320
     GACGCCGTCGATTTCGTCGCTTCATGCCGCAACCATGAGGCCGCCGTCGTCGACGATTTC

A  A  A  K  A  A  K  Y  G  V  G  T  P  A  A  A  A  K  A

1321 CAGCGGCTAAAGCAGCGCAGTTCGGACTAGTTCCGGGCGTAGGTGTTGCGCCAGGTGTTG  1380
     GTCGCCGATTTCGTCGCGTCAAGCCTGATCAAGGCCCGCATCCACAACGCGGTCCACAAC

```
381 GCGTAGCACCGGGTGTTGGTGTTGCTCCGGGCGTAGGTCTGGCACCGGGTGTTGGCGTTG         1440
    CGCATCGTGGCCCACAACCACAACGAGGCCCGCATCCAGACCGTGGCCCACAACCGCAAC

V   A   P   G   V   G   V   A   P   G   V   L   A   P   G   V   G   V   A

441 CACCAGGTGTAGGTGTTGCGCCGGGCGTTGGTGTAGCACCGGGTATCGGTCCGGGTGGCG         1500
    GTGGTCCACATCCACAACGCGGCCCGCAACCACATCGTGGCCCATAGCCAGGCCCACCGC

P   G   V   G   V   A   P   G   V   G   V   A   P   G   I   G   P   G   V

501 TTGCGGCTGCTGCGAAATCTGCTGCGAAGGTTGCTGCGAAAGCGCAGCTGCGTGCAGCAG         1560
    AACGCCGACGACGCTTTAGACGACGCTTCCAACGACGCTTTCGCGTCGACGCACGTCGTC

A   A   A   K   S   A   A   K   V   A   A   K   Q   L   R   A   A   A

561 CTGGTCTGGGTGCGGGCATCCCAGGTCTGGGTGTAGGTGTTGGTGTTCCGGGCCTGGGTG         1620
    GACCAGACCCACGCCCGTAGGGTCCAGACCCACATCCACAACCACAAGGCCCGGACCCAC

G   L   G   A   G   I   P   G   L   G   V   G   V   G   V   P   G   L   G   V

621 TAGGTGCAGGGGTACCGGGCCTGGGTGTTGGTGCAGGCGTTCCGGGTTTCGGTGCTGGCG         1680
    ATCCACGTCCCCATGGCCCGGACCCACAACCACGTCCGCAAGGCCCAAAGCCACGACCGC

G   A   G   V   P   G   L   G   V   G   A   G   V   P   G   F   G   A   G   A

681 CGGACGAAGGTGTACGTCGTTCCCTGTCTCCAGAACTGCGTGAAGGTGACCCGTCCTCTT         1740
    GCCTGCTTCCACATGCAGCAAGGGACAGAGGTCTTGACGCACTTCCACTGGGCAGGAGAA

D   E   G   V   R   R   S   L   S   P   E   L   R   E   G   D   P   S   S

741 CCCAGCACCTGCCGTCTACCCCGTCCTCTCCACGTGTTCCGGGCGCGCTGGCTGCTGCGA         1800
    GGGTCGTGGACGGCAGATGGGGCAGGAGAGGTGCACAAGGCCCGCGCGACCGACGACGCT

Q   H   L   P   S   T   P   S   S   P   R   V   P   G   A   L   A   A   A   K

801 AAGCGGCGAAATACGGTGCAGCGGTTCCGGGTGTACTGGGCGGTCTGGGTGCTCTGGGCG         1860
    TTCGCCGCTTTATGCCACGTCGCCAAGGCCCACATGACCCGCCAGACCCACGAGACCCGC

```
861  GTGTTGGTATCCCGGGCGGTGTTGTAGGTGCAGGCCCAGCTGCAGCTGCTGCTGCGGCAA       1920
     CACAACCATAGGGCCCGCCACAACATCCACGTCCGGGTCGACGTCGACGACGACGCCGTT

V  G  I  P  G  G  V  V  G  A  G  P  A  A  A  A  A  A  K

921  AGGCAGCGGCGAAAGCAGCTCAGTTCGGTCTGGTTGGTGCAGCAGGTCTGGGCGGTCTGG       1980
     TCCGTCGCCGCTTTCGTCGAGTCAAGCCAGACCAACCACGTCGTCCAGACCCGCCAGACC

A  A  A  K  A  A  Q  F  G  L  V  G  A  A  G  L  G  G  L  G

981  GTGTTGGCGGTCTGGGTGTACCGGGCGTTGGTGGTCTGGGTGGCATCCCGCCGGCGGCGG       2040
     CACAACCGCCAGACCCACATGGCCCGCAACCACCAGACCCACCGTAGGGCGGCCGCCGCC

V  G  G  L  G  V  P  G  V  G  G  L  G  G  I  P  P  A  A

2041 CAGCTAAAGCGGCTAAATACGGTGCAGCAGGTCTGGGTGGCGTTCTGGGTGGTGCTGGTC      2100
     GTCGATTTCGCCGATTTATGCCACGTCGTCCAGACCCACCGCAAGACCCACCACGACCAG

A  K  A  A  K  Y  G  A  A  G  L  G  G  V  L  G  G  A  G  Q

2101 AGTTCCCACTGGGCGGTGTAGCGGCACGTCCGGGTTTCGGTCTGTCCCCGATCTTCCCAG      2160
     TCAAGGGTGACCCGCCACATCGCCGTGCAGGCCCAAAGCCAGACAGGGGCTAGAAGGGTC

F  P  L  G  G  V  A  A  R  P  G  F  G  L  S  P  I  F  P  G

2161 GCGGTGCATGCCTGGGTAAAGCTTGCGGCCGTAAACGTAAATAATGATAG                 2210
     CGCCACGTACGGACCCATTTCGAACGCCGGCATTTGCATTTATTACTATCCTAG

| No. | SEQUENCE |
|---|---|
| 1 | GATCCATGGGTGGCGTTCCGGGTGCTATCCCGGGTGGCGTTCCGGGTGTGTATTCTACCCAGGCGCGGGTCTGGGTGCACTGGGCGGTG |
| 2 | GTGCGCTGGGCCCGGGTGGTAAACCGGTTCCAGGCGGTCTGGCAGGTGCTGGTCTGGGTGCAGGTCTGGGCGGTTCCCGG |
| 3 | CGGTTACCTTCCCGGGTGCTCTGGTTCCGGGTGGCGTTGCAGACGCAGCTGCTGCGGTACAAAGCGGCAAAGGCAGGTGCGGGTCTGGGCGGGGTAC |
| 4 | CAGGTGTTGGCGGTCTGGGTGTATCTGCTGGCCAGTTGTTCCGCAGCCGGGTGCAGGTGTAAAACCGGGAAAGTTCCAGGTGTTGGTCTGCCGGGCG |
| 5 | TATACCCGGGTGGTGTTCTGCCGGGCGCGCGTTCCCAGGTGTTGGTGTACTGCCCAGCCGGTGCAGGTGTTAAACCGAAGG |
| 6 | CACCAGGTGTAGGCGGCGCGTTCGCGGGTATCCCGGGTGTTGGCCCGGGTGTCCGCAGCCAGGCGTTCCGCTGGGTTACCGATCAAAGCGCCGA |
| 7 | AGCTTCCAGGTGGCTACGGTCTGCCGGTACACCACCGGTAAACTGCCGTACGGTCCGGGTGGCGTAGCAGGTGCTGCGGGTAA |
| 8 | AGCAGGCGTACCCAACCGGTACTGGTGTTGGTCCGCAGGCTGCTGCGGCAGCTGCGGCGAAGGCAGCAGCAAAATTCGGCGCGGGTGCAGC |
| 9 | GGGTGTTCTGCCGGGCGTAGGTGGTGCTGGCGTTCCAGGTGCGATCCCGGGTGTATCGCAGGCGTAGGTACTCCGGC |
| 10 | GGCCGCTGCGGCTGCGGGCAGCTGCGGCGAAAGCAGCTAAATACGGTGCGGCAGCCTGGTTCCGGGTGGTCCAGGCTTCGGT |
| 11 | CCGGGTGTGTAGGCGTTCCGGGTGCTGGTGTTCCAGGCGTAGGTGTTCCAGGTGCGGGCATCCCGGTTGTACCGGGTGTACCGGGTGTACCGGGTCAGGTA |

FIG. 4(a)

12  TCCCGGGCGCTGCGGTTCCAGGTGTTGTATCCCCGGAAGCGGCAGCTAAGCTGCTGCGAAAGCTGCGAAATACGGAGCT

13  CGTCCGGGCGTTGGTGTTGGTGGCATCCCGACCTACGGTGTAGGTGCAGGCGGTTTCCAGGTTCGGCGTTGGTGTTGGTGGCATCCCGGG

14  TGTAGCTGGTGTTCCGTCTCGTGTTGGTGGCGTACCGGGTGTTGGTGGCGTTCCAGGTGTAGGTATCTCCCCGGAAGCGCAGGCAGCTGCGGC

15  AGCTAAAGCAGGAAGTACGGCCGTTGGTACTCCGGCGACCAGCAGCTGCTAAAGCAGCGCTAAAGCAGCGCAGTTCGGA

16  CTAGTTCCGGGCGTAGGTGTTGCGCCAGGTGTTGGCGTAGCACCGGGTGTTGGTGTTGCTCCCGGGCGTAGGTCTGGCACCGGGTGTTGGCGTTG

17  CACCAGGTGTAGGTGTTGCGCCGGGCGTTGGTGTAGCACCGGGTGTTGGTGTAGCACCGGGTATCGGGTCGTGCGGGCTGCTGCGAAATCTGCTGCGAAGGTGCT

18  GCGAAAGCGCAGCTGCGTGCGAGCAGCTGGTCGGTGCGGGCATCCCAGGTGCGGGTGTTGAGGTGTTGGTGTTCCGGGCCTGGTGTAGGTGCAGGGGTAC

19  CGGGCCTGGGTGTTGGTGCAGGCGTTCCGGTGCTGCGGGCTCGGTGCGCGACGAAGGTGTACGCTCGTTCCCTGTCTCCAGAACTGCGT

20  GAAGGTGACCCGTCCTTCCCAGCACCTGCCGTCCTACCCCGTCCTCTCCACGTGTTCCGGGCGCTGCTGCGGCTGCGAAAGCGGCGAAATAC

21  GGTGCAGCGGTTCCGGGTGTACTGGGCGTCTGGGGTCTCTGGGCGTGTTGGTATCCCGGGCGGTGTTGTAGGTGCAGGCCCAGCTGCA

22  GCTGCTGCTGCGGCAAAGGCAGCGGGCGAAAGCAGCTCAGTTCCGGTCGTTCGTTCCGTTCGGTTGGTGCAGCAGGTCTGGCGCGTCGGGTGTTGGCGGTC

23  TGGGTGTACCGGCGTTGGTGGTCTGGGTGGCAGGGGCAGCTAAAGCGGCTAAATACGGTGCAGCAGGTCTGGGTGGCGTTCGGGTGGCGTTCTGGGT

24  GGTGCTGGTCAGTTCCCACTGGGCGGTGTAGCGGCACGTCCCGGGTTTCGGTCGTGCCCCGATCTTCCCAGGCGGTGCATGCCTGGGTAA

25  AGCTTGCGGCCGTAAACGTAAATAATGATAG

FIG. 4(b)

| No. | SEQUENCE |
|---|---|
| 26 | GCGCACCACGCGCCAGTGCACCCAGAGACCGCGCCTGGGTAGAATACACCACCCGGAACGCCACCCGGATAGCACCCGGAACGCCACCCATG |
| 27 | TAACCGCCGGGAACGCGCCCAGACCGCTGCACCCAGACCAGCACCTGCCAGACCGCCTGGAACCGCCTGGAACCGGTTTCAGCGGTTTACCACCCGGGCCCA |
| 28 | CCCGCCCAGACCCGCCACCTGCCTTTGCCCGCTTTGTACCGCAGCAGCTGCCTCTGCAACGCCACCCGGAACCAGAGCACCCGGAAGG |
| 29 | CGGCAGACCAACACCTGGAACTTTGCCCGGTTTACACCTGCACCCGGCTGCGGAACAACTGCCGCCAGCAGATACACCCAGCCGCCAACACCTGGTAC |
| 30 | TGGTGCCTTCGGTTAACACCTGCACGGTCGGAACGCCCGGCAGTACACCAACACCTGGGAAACGCGCGCCCGGCAGAACACCACCCGGGTATACGCC |
| 31 | AGCTTCGGCGCTTTGATCGGGTAACCAGCGGAACGCCTGGCTGCGGACCACCGGAACGCGCCTCAACCCGGATACCCGCGAACGCCCGCCTACACC |
| 32 | CCTGCTTTACCGCAGCACCTGCTACGCACCCGGACCGTACGGCAGTTTACCGGTGGTGTACGGCAGACCGTAGCCACCTGGA |
| 33 | ACACCCGCTGCACCCGGCGCCGAATTTTGCTGCTGCCTTCGCGCAGCTGCCGCAGCCTGCCGGCACCAACACCAGTACCGGTTGGGTAG |
| 34 | GGCCGCCGGAGTACCTACGCCTGCAGCCTGCGATACCACCGAGGATCGCACCGACCGGATGCCCAGCACCCGGAACGCACCCACCTACGCCCGGCAGA |
| 35 | GCCTGGAACCACCCGGAACAGGCCTGCTGCCACCCGTATTTAGCGCTTTCGCCGCAGCTGCCGCAGCCGAGC |
| 36 | CACCCGGTACAACCGGATGCCCGACCTACGCCACCTGGAACACCTACGCCCGGAACACCAGCACCCGGAACGCCTACAACACCCGGACCGAA |
| 37 | CCGTATTTCGCAGCTTTCGCAGCAGCCTTAGCTGCCGCTTCCGGGGATACAACACCTGGAACCGCAGCCCCGGGATACCTG |

FIG. 5(a)

38  ATGCCACCAACACCAAGCGGAAACCGCCTGCACCTACACCGTAGGTCGGATGCCACCAACACCAACGCCCGGACGAGCT

39  GCTGCCTGCGCTTCCGGGAGATACCTACACCTGGAACGCCACCAACACCCGGTACGCCACCAACAGACGGAACACCAGCTACACCCGGG

40  CTAGTCCGAACTGCGCTGCTTTAGCCGCTGCTTTAGCAGCTGCGCCAACGCCGTACTTCGCTGCTGCTTAGCTGCCGCA

41  CTGGTGCAACGCCAACACCCGGTGCCAGACCTACGCCCGGAGCAACACCAACACCCGGTGCTACGCCAACACCTGGCCAACACCTACGCCCGGAA

42  TTTCGCAGCAACCTTCGCAGCAGCCGAGATTCGCAGCAGCCGCAACCCCACCCGGACCGATACCCGGTGCTACACCAACGCCCCGGGCAACACCTACAC

43  CCCTGCACCTACACCCAGGCCCCCGGAACACCAACACCTACACCCAGACCTGGGATGCCCGCACCCAGACCAGCCGTGCTGCACGCAGCTGCGC

44  ACCTTCACGCAGTTCTGGAGACAGGAACGACGTACACCTTCGTCGCGCCAGCACCCAGCACCGAACGCCTGCACCAACACCCAGGCCCGGTAC

45  CGCCGCTTTCGCAGCAGCCCGGAACGCGCCAGCGCCCGGAACACGTGGAGAGGACGGGTAGACGGGTGCTGGAAGAGGACGGGTC

46  GCTGGGCCTGCACCTACAACACCCGCCCGGATACCAACACCGCCCAGAGCACCCAGACCGCCCAGTACACCCGGAACCGTGCACCCGTATTT

47  CACCCAGACCGCCCAACACCCCAGCCGCCCAGACCTGCTGCACCAACCAGACCGAACTGAGCTGCTTTGCCGCTGCCTTTGCCGCAGCAGCTGCA

48  AACGCCACCCAGACCCTGCTGCACCGTATTTAGCCGCCTTTAGCTGCCGCCGCCGGATGCCACCCAGACCCACCAACGCCGGTA

49  AGCTTTACCCAGGCATGCACCGCCCTGGGAAGATCGGGACAGACCGAAACCCGGACGTGCCGCTACACCGCCCAGTGGAACTGACCAGCACCCCAG

50  GATCCTATCATTATTTACGTTTACGGCCGCA

FIG. 5(b)

```
GATCCATGGGTGGCGTTCCGGGTGCTATCCCGGGTGGCGTTCCGGGTGGTGTATTCTACC    60
     A  G  C  T  G  C  T  T     A     T  A  A  C  T  T

CAGGCGCGGGTCTGGGTGCACTGGGCGGTGGTGCGCTGGGCCCGGGTGGTAAACCGCTGA   120
    G  T        C  A  C  T  A  A  A           G  T  A  C     T  T

AACCGGTTCCAGGCGGTCTGGCAGGTGCTGGTCTGGGTGCAGGTCTGGGCGCGTTCCGG    180
  G  A     C  A  G  T  G        C  T  G     G  C     C     C

CGGTTACCTTCCCGGGTGCTCTGGTTCCGGGTGGCGTTGCAGACGCAGCTGCTGCGTACA   240
  A     T     G           G  T     A  G  T     T     A  C  T

AAGCGGCAAAGGCAGGTGCGGGTCTGGGCGGGGTACCAGGTGTTGGCGGTCTGGGTGTAT   300
    T  T     T  C  T  G  T  T  T  C     A     T  CT A  A  G

CTGCTGGCGCAGTTGTTCCGCAGCCGGGTGCAGGTGTAAAACCGGGCAAAGTTCCAGGTG   360
    A  T  G  G     T     T  A  C  A  G  G  T  G     G  G

TTGGTCTGCCGGGCGTATACCCGGGTGGTGTTCTGCCGGGCGCGCGTTTCCCAGGTGTTG   420
  G  G     A  T        A     C  G  C  A  A  T  G     C     G

GTGTACTGCCGGGCGTTCCGACCGGTGCAGGTGTTAAACCGAAGGCACCAGGTGTAGGCG   480
  G- G  C  T  A     C  T  A     A- G  C     T           T

GCGCGTTCGCGGGTATCCCGGGTGTTGGCCCGTTCGGTGGTCCGCAGCCAGGCGTTCCGC   540
  A  T  T  A     A  A     A  C  T  G  A     A  T  A  C  A

TGGGTTACCCGATCAAAGCGCCGAAGCTTCCAGGTGGCTACGGTCTGCCGTACACCACCG   600
    G  T  C        G  C  C        G  T        T  A  C     A
```

FIG. 6(a)

```
601 GTAAACTGCCGTACGGCTACGGTCCGGGTGGCGTAGCAGGTGCTGCGGGTAAAGCAGGCT
      G      C  T     T G C  A A G T     A      C G T T           660

661 ACCCAACCGGTACTGGTGTTGGTCCGCAGGCTGCTGCGGCAGCTGCGGCGAAGGCAGCAG
         A G A G    C C      A A A      G A T A                   720

721 CAAAATTCGGCGCGGGTGCAGCGGGTGTTCTGCCGGGCGTAGGTGGTGCTGGCGTTCCGG
       G    T T A    C A C C T T T A G    T        T              780

781 GTGTTCCAGGTGCGATCCCGGGCATCGGTGGTATCGCAGGCGTAGGTACTCCGGCGGCCG
       C  G T G A T T A T A C          T G    A T A               840

841 CTGCGGCTGCGGCAGCTGCGGCGAAAGCAGCTAAATACGGTGCGGCAGCAGGCCTGGTTC
      A     A   A C T G     C G T A T T         T A G             900

901 CGGGTGGTCCAGGCTTCGGTCCGGGTGTTGTAGGCGTTCCGGGTGCTGGTGTTCCGGGCG
       T  G      T C      A A T T C A A    C    A T               960

961 TAGGTGTTCCAGGTGCGGGCATCCCGGTTGTACCGGGTGCAGGTATCCCGGGCGCTGCGG
      T  C      A T G T A   C A    T G    A T                     1020

1021 TTCCAGGTGTTGTATCCCCGGAAGCGGCAGCTAAGGCTGCTGCGAAAGCTGCGAAATACG
         G    G A A   A T       A    A G A C                      1080

1081 GAGCTCGTCCGGGCGTTGGTGTTGGTGGCATGCCGACCTACGGTGTAGGTGCAGGCGGTT
      G  CA G  C A C A    A    T T T    G T A T G C               1140

1141 TCCCAGGTTTCGGCGTTGGTGTTGGTGGCATCCCGGGTGTAGCTGGTGTTCCGTCTGTTG
      T  C   T T  C A C A T    T A C A   C TAG C                  1200

1201 GTGGCGTACCGGGTGTTGGTGGCGTTCCAGGTGTAGGTATCTCCCCGGAAGCGCAGGCAG
      A T T  C A C A T C G A T C T      C T                       1260
```

FIG. 6(b)

```
1261  CTGCGGCAGCTAAAGCAGCGAAGTACGGCGTTGGTACTCCGGCGGCAGCAGCTGCTAAAG  1320
         A  T  C  C  G T C        A  G  G  C  A  A  T

1321  CAGCGGCTAAAGCAGCGCAGTTCGGACTAGTTCCGGGCGTAGGTGTTGCGCCAGGTGTTG  1380
         C  C     C  C     T  GT        T  T  C  C  G  T  T  A

1381  GCGTAGCACCGGGTGTTGGTGTTGCTCCGGGCGTAGGTCTGGCACCGGGTGTTGGCGTTG  1440
         G  T  T     C     G        T  A  T CT    T  T  A        G

1441  CACCAGGTGTAGGTGTTGCGCCGGGCGTTGGTGTAGCACCGGGTATCGGTCCGGGTGGCG  1500
         T  T  A  T        G  T  T           C  G  T  C  C  T  C  T        A

1501  TTGCGGCTGCTGCGAAATCTGCTGCGAAGGTTGCTGCGAAAGCGCAGCTGCGTGCAGCAG  1560
            A       A  A     C        C     G     C        C     C  A  T

1561  CTGGTCTGGGTGCGGGCATCCCAGGTCTGGGTGTAGGTGTTGGTGTTCCGGGCCTGGGTG  1620
         G  T     T        T  A  T  A  T        C  C  C  T  A  T  A

1621  TAGGTGCAGGGGTACCGGGCCTGGGTGTTGGTGCAGGCGTTCCGGGTTTCGGTGCTGGCG  1680
         T     T  T  T  A  T  A        T  T     T  C        G  A  T

1681  CGGACGAAGGTGTACGTCGTTCCCTGTCTCCAGAACTGCGTGAAGGTGACCCGTCCTCTT  1740
         A  T  G  A  TA G  GAG        C  T  G  CA G     A  T  C     C

1741  CCCAGCACCTGCCGTCTACCCCGTCCTCTCCACGTGTTCCGGGCGCGCTGGCTGCTGCGA  1800
         T        C  CAGC     C  A  A  CA G  A  T  A  C        C  T

1801  AAGCGGCGAAATACGGTGCAGCGGTTCCGGGTGTACTGGGCGGTCTGGGTGCTCTGGGCG  1860
         A  C     T  A        A  G  T  G  C  T  A  G  C  G        C  T

1861  GTGTTGGTATCCCGGGCGGTGTTGTAGGTGCAGGCCCAGCTGCAGCTGCTGCTGCGGCAA  1920
         A  A  C     A        G  G  A  C  A  C  C  C        C  A  C
```

FIG. 6(c)

```
1921  AGGCAGCGGCGAAAGCAGCTCAGTTCGGTCTGGTTGGTGCAGCAGGTCTGGGCGGTCTGG  1960
         A  T  T  C     C  C        T  C  A  G  A  C  T  G  C  A  A  C

1981  GTGTTGGCGGTCTGGGTGTACCGGGCGTTGGTGGTCTGGGTGGCATCCCGCCGGCGGCGG  2040
         A  C  A  G  T  A  T  A  T        G  C  T  A  T  A  T  A  T  A

2041  CAGCTAAAGCGGCTAAATACGGTGCAGCAGGTCTGGGTGGCGTTCTGGGTGGTGCTGGTC  2100
         C           A                    T  T  C  T  A  T  C  A  G     C  G

2101  AGTTCCCACTGGGCGGTGTAGCGGCACGTCCGGGTTTCGGTCTGTCCCCGATCTTCCCAG  2160
            T  A  A  G  A  A  A  T  C        AT     T  C  T

2161  GCGGTGCATGCCTGGGTAAAGCTTGCGGCCGTAAACGTAAATAATGATAG  2210
         T  G  C        G        T        G  GA  A     G
```

FIG. 6(d)

pND211 (4045 bp)
<u>EcoR1</u>

```
TTCACTGGCC GTCGTTTTAC AACGTCGTGA CTGGGAAAAC CCTGGCGTTA
CCCAACTTAA TCGCCTTGCA GCACATCCCC CTTTCGCCAG CTGGCGTAAT
AGCGAAGAGG CCCGCACCGA TCGCCCTTCC CAACAGTTGC GCAGCCTGAA
TGGCGAATGG CGCCTGATGC GGTATTTTCT CCTTACGCAT CTGTGCGGTA
TTTCACACCG CATATGGTGC ACTCTCAGTA CAATCTGCTC TGATGCCGCA
TAGTTAAGCC AGCCCCGACA CCCGCCAACA CCCGCTGACG CGCCCTGACG
GGCTTGTCTG CTCCCGGCAT CCGCTTACAG ACAAGCTGTG ACCGTCTCCG
GGAGCTGCAT GTGTCAGAGG TTTTCACCGT CATCACCGAA ACGCGCGAGA
CGAAAGGGCC TCGTGATACG CCTATTTTTA TAGGTTAATG TCATGATAAT
AATGGTTTCT TAGACGTCAG GTGGCACTTT TCGGGGAAAT GTGCGCGGAA
CCCCTATTTG TTTATTTTTC TAAATACATT CAAATATGTA TCCGCTCATG
AGACAATAAC CCTGATAAAT GCTTCAATAA TATTGAAAAA GGAAGAGTAT
GAGTATTCAA CATTTCCGTG TCGCCCTTAT TCCCTTTTTT GCGGCATTTT
GCCTTCCTGT TTTTGCTCAC CCAGAAACGC TGGTGAAAGT AAAAGATGCT
GAAGATCAGT TGGGTGCACG AGTGGGTTAC ATCGAACTGG ATCTCAACAG
CGGTAAGATC CTTGAGAGTT TTCGCCCCGA AGAACGTTTT CCAATGATGA
GCACTTTTAA AGTTCTGCTA TGTGGCGCGG TATTATCCCG TATTGACGCC
GGGCAAGAGC AACTCGGTCG CCGCATACAC TATTCTCAGA ATGACTTGGT
TGAGTACTCA CCAGTCACAG AAAAGCATCT TACGGATGGC ATGACAGTAA
GAGAATTATG CAGTGCTGCC ATAACCATGA GTGATAACAC TGCGGCCAAC
TTACTTCTGA CAACGATCGG AGGACCGAAG GAGCTAACCG CTTTTTTGCA
CAACATGGGG GATCATGTAA CTCGCCTTGA TCGTTGGGAA CCGGAGCTGA
ATGAAGCCAT ACCAAACGAC GAGCGTGACA CCACGATGCC TGTAGCAATG
GCAACAACGT TGCGCAAACT ATTAACTGGC GAACTACTTA CTCTAGCTTC
CCGGCAACAA TTAATAGACT GGATGGAGGC GGATAAAGTT GCAGGACCAC
TTCTGCGCTC GGCCCTTCCG GCTGGCTGGT TTATTGCTGA TAAATCTGGA
GCCGGTGAGC GTGGGTCTCG CGGTATCATT GCAGCACTGG GGCCAGATGG
TAAGCCCTCC CGTATCGTAG TTATCTACAC GACGGGGAGT CAGGCAACTA
TGGATGAACG AAATAGACAG ATCGCTGAGA TAGGTGCCTC ACTGATTAAG
CATTGGTAAC TGTCAGACCA AGTTTACTCA TATATACTTT AGATTGATTT
AAAACTTCAT TTTTAATTTA AAAGGATCTA GGTGAAGATC CTTTTTGATA
ATCTCATGAC CAAAATCCCT TAACGTGAGT TTTCGTTCCA CTGAGCGTCA
GACCCCGTAG AAAAGATCAA AGGATCTTCT TGAGATCCTT TTTTTCTGCG
CGTAATCTGC TGCTTGCAAA CAAAAAAACC ACCGCTACCA GCGGTGGTTT
GTTTGCCGGA TCAAGAGCTA CCAACTCTTT TTCCGAAGGT AACTGGCTTC
AGCAGAGCGC AGATACCAAA TACTGTTCTT CTAGTGTAGC CGTAGTTAGG
CCACCACTTC AAGAACTCTG TAGCACCGCC TACATACCTC GCTCTGCTAA
TCCTGTTACC AGTGGCTGCT GCCAGTGGCG ATAAGTCGTG TCTTACCGGG
TTGGACTCAA GACGATAGTT ACCGGATAAG GCGCAGCGGT CGGGCTGAAC
GGGGGGTTCG TGCACACAGC CCAGCTTGGA GCGAACGACC TACACCGAAC
TGAGATACCT ACAGCGTGAG CATTGAGAAA GCGCCACGCT TCCCGAAGGG
AGAAAGGCGG ACAGGTATCC GGTAAGCGGC AGGGTCGGAA CAGGAGAGCG
CACGAGGGAG CTTCCAGGGG GAAACGCCTG GTATCTTTAT AGTCCTGTCG
GGTTTCGCCA CCTCTGACTT GAGCGTCGAT TTTTGTGATG CTCGTCAGGG
```

<i>bla</i>

FIG. 9(a)

```
GGGCGGAGCC TATGGAAAAA CGCCAGCAAC GCGGCCTTTT TACGGTTCCT
GGCCTTTTGC TGGCCTTTTG CTCACATGTT CTTTCCTGCG TTATCCCCTG
ATTCTGTGGA TAACCGTATT ACCGCCTTTG AGTGAGCTGA TACCGCTCGC
CGCAGCCGAA CGACCGAGCG CAGCGAGTCA GTGAGCGAGG AAGCGGAAGA
GCGCCCAATA CGCAAACCGC CTCTCCCGC GCGTTGGCCG ATTCATTAAT
GCAGCTGGCA CGACAGGTTT CCCGACTGGA AAGCGGGCAG TGAGCGCAAC
GCAATTAATG TGAGTTAGCT CACTCATTAG GCACCCCAGG CTTTACACTT   plac-35
TATGCTTCCG GCTCGTATGT TGTGTGGAAT TGTGAGCGGA TAACAATTTC
ACACAGGAAA CAGCTATGAC CATGATTACG CCAAGCTTGG CTGCAGGTGA
TGATTATCAG CCAGCAGAGA TTAAGGAAAA CAGACAGGTT TATTGAGCGC
TTATCTTTCC CTTTATTTTT GCTGCGGTAA GTCGCATAAA AACCATTCTT
CATAATTCAA TCCATTTACT ATGTTATGTT CTGAGGGGAG TGAAAATTCC
CCTAATTCGA TGAAGATTCT TGCTCAATTG TTATCAGCTA TGCGCCGACC
AGAACACCTT GCCGATCAGC CAAACGTCTC TTCAGGCCAC TGACTAGCGA
TAACTTTCCC CACAACGGAA CAACTCTCAT TGCATGGGAT CATTGGGTAC
TGTGGGTTTA GTGGTTGTAA AAACACCTGA CCGCTATCCC TGATCAGTTT
CTTGAAGGTA AACTCATCAC CCCCAAGTCT GGCTATGCAG AAATCACCTG
GCTCAACAGC CTGCTCAGGG TCAACGAGAA TTAACATTCC GTCAGGAAAG
CTTGGCTTGG AGCCTGTTGG TGCGGTCATG GAATTACCTT CAACCTCAAG
CCAGAATGCA GAATCACTGG CTTTTTTGGT TGTGCTTACC CATCTCTCCG
CATCACCTTT GGTAAAGGTT CTAAGCTTAG GTGAGAACAT CCCTGCCTGA
ACATGAGAAA AAACAGGGTA CTCATACTCA CTTCTAAGTG ACGGCTGCAT
ACTAACCGCT TCATACATCT CGTAGATTTC TCTGGCGATT GAAGGGCTAA
ATTCTTCAAC GCTAACTTTG AGAATTTTTG CAAGCAATGC GGCGTTATAA
GCATTTAATG CATTGATGCC ATTAAATAAA GCACCAACGC CTGACTGCCC   cI857
CATCCCCATC TTGTCTGCGA CAGATTCCTG GGATAAGCCA AGTTCATTTT
TCTTTTTTTC ATAAATTGCT TTAAGGCGAC GTGCGTCCTC AAGCTGCTCT
TGTGTTAATG GTTTCTTTTT TGTGCTCATA CGTTAAATCT ATCACCGCAA
GGGATAAATA TCTAACACCG TGCGTGTTGA CTATTTTACC TCTGGCGGTG
ATAATGGTTG CATGTACTAA GGAGGTTGTA TGGAACAACG CATAACCCTG
AAAGATTATG CAATGCGCTT TGGGCAAACC AAGACAGCTA AAGATCTCTC
ACCTACCAAA CAATGCCCCC CTGCAAAAAA TAAATTCATA TAAAAAACAT
ACAGATAACC ATCTGCGGTG ATAAATTATC TCTGGCGGTG TTGACATAAA
TACCACTGGC GGTGATACTG AGCACATCAG CAGGACGCAC TGACCACCAT
GAAGGTGACG CTCTTAAAAA TTAAGCCCTG AAGAAGGGCA GCATTCAAAG
CAGAAGGCTT TGGGGTGTGT GATACGAAAC GAAGCATTGG GATCCTAAGG   RBS
AGGTTTAAGA TCCATGGTT TAAACCTCCT TAGGATCCCC GGGAA-EcoRI
           NcoI                               BamHI
```

FIG. 9(b)

SEQUENCE LISTING (1) GENERAL INFORMATION:

(iii) NUMBER OF SEQUENCES: 54

(2) INFORMATION FOR SEQ ID NO:1:

(i) SEQUENCE CHARACTERISTICS:
      (A) LENGTH: 2210 base pairs
      (B) TYPE: nucleic acid
      (C) STRANDEDNESS: double
      (D) TOPOLOGY: linear (iii) HYPOTHETICAL: YES (iv) ANTI-SENSE: NO (xi) SEQUENCE DESCRIPTION: SEQ ID NO:1:

```
GATCCATGGG TGGCGTTCCG GGTGCTATCC CGGGTGGCGT TCCGGGTGGT GTATTCTACC      60

CAGGCGCGGG TCTGGGTGCA CTGGGCGGTG GTGCGCTGGG CCCGGGTGGT AAACCGCTGA     120

AACCGGTTCC AGGCGGTCTG GCAGGTGCTG GTCTGGGTGC AGGTCTGGGC GCGTTCCCGG     180

CGGTTACCTT CCCGGGTGCT CTGGTTCCGG GTGGCGTTGC AGACGCAGCT GCTGCGTACA     240

AAGCGGCAAA GGCAGGTGCG GGTCTGGGCG GGTACCAGG TGTTGGCGGT CTGGGTGTAT     300

CTGCTGGCGC AGTTGTTCCG CAGCCGGGTG CAGGTGTAAA ACCGGGCAAA GTTCCAGGTG     360

TTGGTCTGCC GGGCGTATAC CCGGGTGGTG TTCTGCCGGG CGCGCGTTTC CCAGGTGTTG     420

GTGTACTGCC GGGCGTTCCG ACCGGTGCAG GTGTTAAACC GAAGGCACCA GGTGTAGGCG     480

GCGCGTTCGC GGGTATCCCG GGTGTTGGCC CGTTCGGTGG TCCGCAGCCA GGCGTTCCGC     540

TGGGTTACCC GATCAAAGCG CCGAAGCTTC AGGTGGCTA CGGTCTGCCG TACACCACCG     600

GTAAACTGCC GTACGGCTAC GGTCCGGGTG GCGTAGCAGG TGCTGCGGGT AAAGCAGGCT     660

ACCCAACCGG TACTGGTGTT GGTCCGCAGG CTGCTGCGGC AGCTGCGGCG AAGGCAGCAG     720

CAAAATTCGG CGCGGGTGCA GCGGGTGTTC TGCCGGGCGT AGGTGGTGCT GGCGTTCCGG     780

GTGTTCCAGG TGCGATCCCG GGCATCGGTG GTATCGCAGG CGTAGGTACT CCGGCGGCCA     840

CTGCGGCTGC GGCAGCTGCG GCGAAAGCAG CTAAATACGG TGCGGCAGCA GGCCTGGTTC     900

CGGGTGGTCC AGGCTTCGGT CCGGGTGTTG TAGGCGTTCC GGGTGCTGGT GTTCCGGGCG     960

TAGGTGTTCC AGGTGCGGGC ATCCCGGTTG TACCGGGTGC AGGTATCCCG GGCGCTGCGG    1020

TTCCAGGTGT TGTATCCCCG GAAGCGGCAG CTAAGGCTGC TGCGAAAGCT GCGAAATACG    1080

GAGCTCGTCC GGGCGTTGGT GTTGGTGGCA TCCCGACCTA CGGTGTAGGT GCAGGCGGTT    1140
```

-continued

```
TCCCAGGTTT CGGCGTTGGT GTTGGTGGCA TCCCGGGTGT AGCTGGTGTT CCGTCTGTTG    1200

GTGGCGTACC GGGTGTTGGT GGCGTTCCAG GTGTAGGTAT CTCCCCGGAA GCGCAGGCAG    1260

CTGCGGCAGC TAAAGCAGCG AAGTACGGCG TTGGTACTCC GGCGGCAGCA GCTGCTAAAG    1320

CAGCGGCTAA AGCAGCGCAG TTCGGACTAG TTCCGGGCGT AGGTGTTGCG CCAGGTGTTG    1380

GCGTAGCACC GGGTGTTGGT GTTGCTCCGG GCGTAGGTCT GGCACCGGGT GTTGGCGTTG    1440

CACCAGGTGT AGGTGTTGCG CCGGGCGTTG GTGTAGCACC GGGTATCGGT CCGGGTGGCG    1500

TTGCGGCTGC TGCGAAATCT GCTGCGAAGG TTGCTGCGAA AGCGCAGCTG CGTGCAGCAG    1560

CTGGTCTGGG TGCGGGCATC CCAGGTCTGG GTGTAGGTGT TGGTGTTCCG GGCCTGGGTG    1620

TAGGTGCAGG GGTACCGGGC CTGGGTGTTG GTGCAGGCGT TCCGGGTTTC GGTGCTGGCG    1680

CGGACGAAGG TGTACGTCGT TCCCTGTCTC CAGAACTGCG TGAAGGTGAC CCGTCCTCTT    1740

CCCAGCACCT GCCGTCTACC CCGTCCTCTC CACGTGTTCC GGGCGCGCTG GCTGCTGCGA    1800

AAGCGGCGAA ATACGGTGCA GCGGTTCCGG GTGTACTGGG CGGTCTGGGT GCTCTGGGCG    1860

GTGTTGGTAT CCCGGGCGGT GTTGTAGGTG CAGGCCCAGC TGCAGCTGCT GCTGCGGCAA    1920

AGGCAGCGGC GAAAGCAGCT CAGTTCGGTC TGGTTGGTGC AGCAGGTCTG GGCGGTCTGG    1980

GTGTTGGCGG TCTGGGTGTA CCGGGCGTTG GTGGTCTGGG TGGCATCCCG CCGGCGGCGG    2040

CAGCTAAAGC GGCTAAATAC GGTGCAGCAG GTCTGGGTGG CGTTCTGGGT GGTGCTGGTC    2100

AGTTCCCACT GGGCGGTGTA GCGGCACGTC CGGGTTTCGG TCTGTCCCCG ATCTTCCCAG    2160

GCGGTGCATG CCTGGGTAAA GCTTGCGGCC GTAAACGTAA ATAATGATAG               2210
```

(2) INFORMATION FOR SEQ ID NO:2:

(i) SEQUENCE CHARACTERISTICS:
        (A) LENGTH: 733 amino acids
        (B) TYPE: amino acid
        (D) TOPOLOGY: linear (ii) MOLECULE TYPE: protein (xi) SEQUENCE DESCRIPTION: SEQ ID NO:2:

```
Ser Met Gly Gly Val Pro Gly Ala Ile Pro Gly Gly Val Pro Gly Gly
1               5                   10                  15

Val Phe Tyr Pro Gly Ala Gly Leu Gly Ala Leu Gly Gly Gly Ala Leu
            20                  25                  30

Gly Pro Gly Gly Lys Pro Leu Lys Pro Val Pro Gly Gly Leu Ala Gly
        35                  40                  45

Ala Gly Leu Gly Ala Gly Leu Gly Ala Phe Pro Ala Val Thr Phe Pro
    50                  55                  60

Gly Ala Leu Val Pro Gly Val Ala Asp Ala Ala Ala Tyr Lys
65                  70                  75                  80

Ala Ala Lys Ala Gly Ala Gly Leu Gly Gly Val Pro Gly Val Gly Gly
                85                  90                  95

Leu Gly Val Ser Ala Gly Ala Val Val Pro Gln Pro Gly Ala Gly Val
                100                 105                 110

Lys Pro Gly Lys Val Pro Gly Val Gly Leu Pro Gly Val Tyr Pro Gly
            115                 120                 125

Gly Val Leu Pro Gly Ala Arg Phe Pro Gly Val Gly Val Leu Pro Gly
        130                 135                 140

Val Pro Thr Gly Ala Gly Val Lys Pro Lys Ala Pro Gly Val Gly Gly
145                 150                 155                 160
```

-continued

```
Ala Phe Ala Gly Ile Pro Gly Val Gly Pro Phe Gly Pro Gln Pro
            165                 170                 175

Gly Val Pro Leu Gly Tyr Pro Ile Lys Ala Pro Lys Leu Pro Gly Gly
            180                 185                 190

Tyr Gly Leu Pro Tyr Thr Thr Gly Lys Leu Pro Tyr Gly Tyr Gly Pro
            195                 200                 205

Gly Gly Val Ala Gly Ala Gly Lys Ala Gly Tyr Pro Thr Gly Thr
            210                 215                 220

Gly Val Gly Pro Gln Ala Ala Ala Ala Ala Lys Ala Ala
225                 230                 235                 240

Lys Phe Gly Ala Gly Ala Ala Gly Val Leu Pro Gly Val Gly Gly Ala
            245                 250                 255

Gly Val Pro Gly Val Pro Gly Ala Ile Pro Gly Ile Gly Ile Ala
            260                 265                 270

Gly Val Gly Thr Pro Ala Ala Ala Ala Ala Ala Ala Ala Lys
            275                 280                 285

Ala Ala Lys Tyr Gly Ala Ala Gly Leu Val Pro Gly Gly Pro Gly
            290                 295                 300

Phe Gly Pro Gly Val Val Gly Val Pro Gly Ala Gly Val Pro Gly Val
305                 310                 315                 320

Gly Val Pro Gly Ala Gly Ile Pro Val Val Pro Gly Ala Gly Ile Pro
            325                 330                 335

Gly Ala Ala Val Pro Gly Val Val Ser Pro Glu Ala Ala Lys Ala
            340                 345                 350

Ala Ala Lys Ala Ala Lys Tyr Gly Ala Arg Pro Gly Val Gly Val Gly
            355                 360                 365

Gly Ile Pro Thr Tyr Gly Val Gly Ala Gly Gly Phe Pro Gly Phe Gly
            370                 375                 380

Val Gly Val Gly Gly Ile Pro Gly Val Ala Gly Val Pro Ser Val Gly
385                 390                 395                 400

Gly Val Pro Gly Val Gly Gly Val Pro Gly Val Gly Ile Ser Pro Glu
            405                 410                 415

Ala Gln Ala Ala Ala Ala Lys Ala Ala Lys Tyr Gly Val Gly Thr
            420                 425                 430

Pro Ala Ala Ala Ala Lys Ala Ala Lys Ala Ala Gln Phe Gly
            435                 440                 445

Leu Val Pro Gly Val Gly Val Ala Pro Gly Val Gly Val Ala Pro Gly
            450                 455                 460

Val Gly Val Ala Pro Gly Val Gly Leu Ala Pro Gly Val Gly Val Ala
465                 470                 475                 480

Pro Gly Val Gly Val Ala Pro Gly Val Gly Val Ala Pro Gly Ile Gly
            485                 490                 495

Pro Gly Gly Val Ala Ala Ala Lys Ser Ala Ala Lys Val Ala Ala
            500                 505                 510

Lys Ala Gln Leu Arg Ala Ala Gly Leu Gly Ala Gly Ile Pro Gly
            515                 520                 525

Leu Gly Val Gly Val Gly Val Pro Gly Leu Gly Val Gly Ala Gly Val
            530                 535                 540

Pro Gly Leu Gly Val Gly Ala Gly Val Pro Gly Phe Gly Ala Gly Ala
545                 550                 555                 560

Asp Glu Gly Val Arg Arg Ser Leu Ser Pro Glu Leu Arg Glu Gly Asp
            565                 570                 575

Pro Ser Ser Ser Gln His Leu Pro Ser Thr Pro Ser Ser Pro Arg Val
```

```
                580             585             590
Pro Gly Ala Leu Ala Ala Ala Lys Ala Ala Lys Tyr Gly Ala Ala Val
            595             600             605
Pro Gly Val Leu Gly Gly Leu Gly Ala Leu Gly Val Gly Ile Pro
    610             615             620
Gly Gly Val Val Gly Ala Gly Pro Ala Ala Ala Ala Ala Ala Lys
625             630             635             640
Ala Ala Ala Lys Ala Ala Gln Phe Gly Leu Val Gly Ala Ala Gly Leu
                645             650             655
Gly Gly Leu Gly Val Gly Gly Leu Gly Val Pro Gly Val Gly Gly Leu
            660             665             670
Gly Gly Ile Pro Pro Ala Ala Ala Lys Ala Ala Lys Tyr Gly Ala
            675             680             685
Ala Gly Leu Gly Gly Val Leu Gly Gly Ala Gly Gln Phe Pro Leu Gly
    690             695             700
Gly Val Ala Ala Arg Pro Gly Phe Gly Leu Ser Pro Ile Phe Pro Gly
705             710             715             720
Gly Ala Cys Leu Gly Lys Ala Cys Gly Arg Lys Arg Lys
                725             730
```

(2) INFORMATION FOR SEQ ID NO:3:

(i) SEQUENCE CHARACTERISTICS:
        (A) LENGTH: 90 base pairs
        (B) TYPE: nucleic acid
        (C) STRANDEDNESS: single
        (D) TOPOLOGY: linear (iii) HYPOTHETICAL: YES (iv) ANTI-SENSE: NO (xi) SEQUENCE DESCRIPTION: SEQ ID NO:3:

```
GATCCATGGG TGGCGTTCCG GGTGCTATCC CGGGTGGCGT TCCGGGTGGT GTATTCTACC    60

CAGGCGCGGG TCTGGGTGCA CTGGGCGGTG                                    90
```

(2) INFORMATION FOR SEQ ID NO:4:

(i) SEQUENCE CHARACTERISTICS:
        (A) LENGTH: 90 base pairs
        (B) TYPE: nucleic acid
        (C) STRANDEDNESS: single
        (D) TOPOLOGY: linear (iii) HYPOTHETICAL: YES (iv) ANTI-SENSE: NO (xi) SEQUENCE DESCRIPTION: SEQ ID NO:4:

```
GTGCGCTGGG CCCGGGTGGT AAACCGCTGA AACCGGTTCC AGGCGGTCTG GCAGGTGCTG    60

GTCTGGGTGC AGGTCTGGGC GCGTTCCCGG                                    90
```

(2) INFORMATION FOR SEQ ID NO:5:

(i) SEQUENCE CHARACTERISTICS:
        (A) LENGTH: 96 base pairs
        (B) TYPE: nucleic acid
        (C) STRANDEDNESS: single
        (D) TOPOLOGY: linear (iii) HYPOTHETICAL: YES (iv) ANTI-SENSE: NO (xi) SEQUENCE DESCRIPTION: SEQ ID NO:5:

CGGTTACCTT CCCGGGTGCT CTGGTTCCGG GTGGCGTTGC AGACGCAGCT GCTGCGTACA    60

AAGCGGCAAA GGCAGGTGCG GGTCTGGGCG GGGTAC    96

(2) INFORMATION FOR SEQ ID NO:6:

(i) SEQUENCE CHARACTERISTICS:
        (A) LENGTH: 99 base pairs
        (B) TYPE: nucleic acid
        (C) STRANDEDNESS: single
        (D) TOPOLOGY: linear (iii) HYPOTHETICAL: YES (iv) ANTI-SENSE: NO (xi) SEQUENCE DESCRIPTION: SEQ ID NO:6:

CAGGTGTTGG CGGTCTGGGT GTATCTGCTG GCGCAGTTGT TCCGCAGCCG GGTGCAGGTG    60

TAAAACCGGG CAAAGTTCCA GGTGTTGGTC TGCCGGGCG    99

(2) INFORMATION FOR SEQ ID NO:7:

(i) SEQUENCE CHARACTERISTICS:
        (A) LENGTH: 90 base pairs
        (B) TYPE: nucleic acid
        (C) STRANDEDNESS: single
        (D) TOPOLOGY: linear (iii) HYPOTHETICAL: YES (iv) ANTI-SENSE: NO (xi) SEQUENCE DESCRIPTION: SEQ ID NO:7:

TATACCCGGG TGGTGTTCTG CCGGGCGCGC GTTTCCCAGG TGTTGGTGTA CTGCCGGGCG    60

TTCCGACCGG TGCAGGTGTT AAACCGAAGG    90

(2) INFORMATION FOR SEQ ID NO:8:

(i) SEQUENCE CHARACTERISTICS:
        (A) LENGTH: 99 base pairs
        (B) TYPE: nucleic acid
        (C) STRANDEDNESS: single
        (D) TOPOLOGY: linear (iii) HYPOTHETICAL: YES (iv) ANTI-SENSE: NO (xi) SEQUENCE DESCRIPTION: SEQ ID NO:8:

CACCAGGTGT AGGCGGCGCG TTCGCGGGTA TCCCGGGTGT TGGCCCGTTC GGTGGTCCGC    60

AGCCAGGCGT TCCGCTGGGT TACCCGATCA AAGCGCCGA    99

(2) INFORMATION FOR SEQ ID NO:9:

(i) SEQUENCE CHARACTERISTICS:
        (A) LENGTH: 88 base pairs
        (B) TYPE: nucleic acid
        (C) STRANDEDNESS: single
        (D) TOPOLOGY: linear (iii) HYPOTHETICAL: YES (iv) ANTI-SENSE: NO (xi) SEQUENCE DESCRIPTION: SEQ ID NO:9:

```
AGCTTCCAGG TGGCTACGGT CTGCCGTACA CCACCGGTAA ACTGCCGTAC GGCTACGGTC      60

CGGGTGGCGT AGCAGGTGCT GCGGGTAA                                        88

(2) INFORMATION FOR SEQ ID NO:10:

(i) SEQUENCE CHARACTERISTICS:
        (A) LENGTH: 90 base pairs
        (B) TYPE: nucleic acid
        (C) STRANDEDNESS: single
        (D) TOPOLOGY: linear (iii) HYPOTHETICAL: YES (iv) ANTI-SENSE: NO (xi) SEQUENCE DESCRIPTION: SEQ ID NO:10:

AGCAGGCTAC CAACCGGTA CTGGTGTTGG TCCGCAGGCT GCTGCGGCAG CTGCGGCGAA       60

GGCAGCAGCA AAATTCGGCG CGGGTGCAGC                                      90

(2) INFORMATION FOR SEQ ID NO:11:

(i) SEQUENCE CHARACTERISTICS:
        (A) LENGTH: 93 base pairs
        (B) TYPE: nucleic acid
        (C) STRANDEDNESS: single
        (D) TOPOLOGY: linear (iii) HYPOTHETICAL: YES (iv) ANTI-SENSE: NO (xi) SEQUENCE DESCRIPTION: SEQ ID NO:11:

GGGTGTTCTG CCGGGCGTAG GTGGTGCTGG CGTTCCGGGT GTTCCAGGTG CGATCCCGGG      60

CATCGGTGGT ATCGCAGGCG TAGGTACTCC GGC                                  93

(2) INFORMATION FOR SEQ ID NO:12:

(i) SEQUENCE CHARACTERISTICS:
        (A) LENGTH: 85 base pairs
        (B) TYPE: nucleic acid
        (C) STRANDEDNESS: single
        (D) TOPOLOGY: linear (iii) HYPOTHETICAL: YES (iv) ANTI-SENSE: NO (xi) SEQUENCE DESCRIPTION: SEQ ID NO:12:

GGCCGCTGCG GCTGCGGCAG CTGCGGCGAA AGCAGCTAAA TACGGTGCGG CAGCAGCCT       60

GGTTCCGGGT GGTCCAGGCT TCGGT                                           85

(2) INFORMATION FOR SEQ ID NO:13:

(i) SEQUENCE CHARACTERISTICS:
        (A) LENGTH: 85 base pairs
        (B) TYPE: nucleic acid
        (C) STRANDEDNESS: single
        (D) TOPOLOGY: linear (iii) HYPOTHETICAL: YES (iv) ANTI-SENSE: NO (xi) SEQUENCE DESCRIPTION: SEQ ID NO:13:

CCGGGTGTTG TAGGCGTTCC GGGTGCTGGT GTTCCGGGCG TAGGTGTTCC AGGTGCGGC       60

ATCCCGGTTG TACCGGGTGC AGGTA                                           85
```

(2) INFORMATION FOR SEQ ID NO:14:

(i) SEQUENCE CHARACTERISTICS:
        (A) LENGTH: 80 base pairs
        (B) TYPE: nucleic acid
        (C) STRANDEDNESS: single
        (D) TOPOLOGY: linear (iii) HYPOTHETICAL: YES (iv) ANTI-SENSE: NO (xi) SEQUENCE DESCRIPTION: SEQ ID NO:14:

```
TCCCGGGCGC TGCGGTTCCA GGTGTTGTAT CCCCGGAAGC GGCAGCTAAG GCTGCTGGA      60

AAGCTGCGAA ATACGGAGCT                                                80
```

(2) INFORMATION FOR SEQ ID NO:15:

(i) SEQUENCE CHARACTERISTICS:
        (A) LENGTH: 92 base pairs
        (B) TYPE: nucleic acid
        (C) STRANDEDNESS: single
        (D) TOPOLOGY: linear (iii) HYPOTHETICAL: YES (iv) ANTI-SENSE: NO (xi) SEQUENCE DESCRIPTION: SEQ ID NO:15:

```
CGTCCGGGCG TTGGTGTTGG TGGCATCCCG ACCTACGGTG TAGGTGCAGG CGGTTTCCA       60

GGTTTCGGCG TTGGTGTTGG TGGCATCCCG GG                                   92
```

(2) INFORMATION FOR SEQ ID NO:16:

(i) SEQUENCE CHARACTERISTICS:
        (A) LENGTH: 90 base pairs
        (B) TYPE: nucleic acid
        (C) STRANDEDNESS: single
        (D) TOPOLOGY: linear (iii) HYPOTHETICAL: YES (iv) ANTI-SENSE: NO (xi) SEQUENCE DESCRIPTION: SEQ ID NO:16:

```
TGTAGCTGGT GTTCCGTCTG TTGGTGGCGT ACCGGGTGTT GGTGGCGTTC CAGGTGTAG       60

TATCTCCCCG GAAGCGCAGG CAGCTGCGGC                                      90
```

(2) INFORMATION FOR SEQ ID NO:17:

(i) SEQUENCE CHARACTERISTICS:
        (A) LENGTH: 79 base pairs
        (B) TYPE: nucleic acid
        (C) STRANDEDNESS: single
        (D) TOPOLOGY: linear (iii) HYPOTHETICAL: YES (iv) ANTI-SENSE: NO (xi) SEQUENCE DESCRIPTION: SEQ ID NO:17:

```
AGCTAAAGCA GCGAAGTACG GCGTTGGTAC TCCGGCGGCA GCAGCTGCTA AAGCAGCGGC      60

TAAAGCAGCG CAGTTCGGA                                                  79
```

(2) INFORMATION FOR SEQ ID NO:18:

(i) SEQUENCE CHARACTERISTICS:
        (A) LENGTH: 94 base pairs
        (B) TYPE: nucleic acid
        (C) STRANDEDNESS: single
        (D) TOPOLOGY: linear (iii) HYPOTHETICAL: YES (iv) ANTI-SENSE: NO (xi) SEQUENCE DESCRIPTION: SEQ ID NO:18:

CTAGTTCCGG GCGTAGGTGT TGCGCCAGGT GTTGGCGTAG CACCGGGTGT TGGTGTTGCT        60

CCGGGCGTAG GTCTGGCACC GGGTGTTGGC GTTG        94

(2) INFORMATION FOR SEQ ID NO:19:

(i) SEQUENCE CHARACTERISTICS:
        (A) LENGTH: 95 base pairs
        (B) TYPE: nucleic acid
        (C) STRANDEDNESS: single
        (D) TOPOLOGY: linear (iii) HYPOTHETICAL: YES (iv) ANTI-SENSE: NO (xi) SEQUENCE DESCRIPTION: SEQ ID NO:19:

CACCAGGTGT AGGTGTTGCG CCGGGCGTTG GTGTAGCACC GGGTATCGGT CCGGGTGGCG        60

TTGCGGCTGC TGCGAAATCT GCTGCGAAGG TTGCT        95

(2) INFORMATION FOR SEQ ID NO:20:

(i) SEQUENCE CHARACTERISTICS:
        (A) LENGTH: 100 base pairs
        (B) TYPE: nucleic acid
        (C) STRANDEDNESS: single
        (D) TOPOLOGY: linear (iii) HYPOTHETICAL: YES (iv) ANTI-SENSE: NO (xi) SEQUENCE DESCRIPTION: SEQ ID NO:20:

GCGAAAGCGC AGCTGCGTGC AGCAGCTGGT CTGGGTGCGG GCATCCCAGG TCTGGGTGTA        60

GGTGTTGGTG TTCCGGGCCT GGGTGTAGGT GCAGGGGTAC        100

(2) INFORMATION FOR SEQ ID NO:21:

(i) SEQUENCE CHARACTERISTICS:
        (A) LENGTH: 86 base pairs
        (B) TYPE: nucleic acid
        (C) STRANDEDNESS: single
        (D) TOPOLOGY: linear (iii) HYPOTHETICAL: YES (iv) ANTI-SENSE: NO (xi) SEQUENCE DESCRIPTION: SEQ ID NO:21:

CGGGCCTGGG TGTTGGTGCA GGCGTTCCGG GTTTCGGTGC TGGCGCGGAC GAAGGTGTC        60

GTCGTTCCCT GTCTCCAGAA CTGCGT        86

(2) INFORMATION FOR SEQ ID NO:22:

(i) SEQUENCE CHARACTERISTICS:
        (A) LENGTH: 93 base pairs (B) TYPE: nucleic acid
            (C) STRANDEDNESS: single
            (D) TOPOLOGY: linear (iii) HYPOTHETICAL: YES (iv) ANTI-SENSE: NO (xi) SEQUENCE DESCRIPTION: SEQ ID NO:22:

GAAGGTGACC CGTCCTCTTC CCAGCACCTG CCGTCTACCC CGTCCTCTCC ACGTGTTCC      60

GGCGCGCTGG CTGCTGCGAA AGCGGCGAAA TAC                                 93

(2) INFORMATION FOR SEQ ID NO:23:

(i) SEQUENCE CHARACTERISTICS:
            (A) LENGTH: 90 base pairs
            (B) TYPE: nucleic acid
            (C) STRANDEDNESS: single
            (D) TOPOLOGY: linear (iii) HYPOTHETICAL: YES (iv) ANTI-SENSE: NO (xi) SEQUENCE DESCRIPTION: SEQ ID NO:23:

GGTGCAGCGG TTCCGGGTGT ACTGGGCGGT CTGGGTGCTC TGGGCGGTGT TGGTATCCCG     60

GGCGGTGTTG TAGGTGCAGG CCCAGCTGCA                                     90

(2) INFORMATION FOR SEQ ID NO:24:

(i) SEQUENCE CHARACTERISTICS:
            (A) LENGTH: 88 base pairs
            (B) TYPE: nucleic acid
            (C) STRANDEDNESS: single
            (D) TOPOLOGY: linear (iii) HYPOTHETICAL: YES (iv) ANTI-SENSE: NO (xi) SEQUENCE DESCRIPTION: SEQ ID NO:24:

GCTGCTGCTG CGGCAAAGGC AGCGGCGAAA GCAGCTCAGT TCGGTCTGGT TGGTGCAGCA     60

GGTCTGGGCG GTCTGGGTGT TGGCGGTC                                       88

(2) INFORMATION FOR SEQ ID NO:25:

(i) SEQUENCE CHARACTERISTICS:
            (A) LENGTH: 98 base pairs
            (B) TYPE: nucleic acid
            (C) STRANDEDNESS: single
            (D) TOPOLOGY: linear (iii) HYPOTHETICAL: YES (iv) ANTI-SENSE: NO (xi) SEQUENCE DESCRIPTION: SEQ ID NO:25:

TGGGTGTACC GGGCGTTGGT GGTCTGGGTG GCATCCCGCC GGCGGCGGCA GCTAAAGCGG     60

CTAAATACGG TGCAGCAGGT CTGGGTGGCG TTCTGGGT                            98

(2) INFORMATION FOR SEQ ID NO:26:

(i) SEQUENCE CHARACTERISTICS:
            (A) LENGTH: 89 base pairs
            (B) TYPE: nucleic acid
            (C) STRANDEDNESS: single
            (D) TOPOLOGY: linear (iii) HYPOTHETICAL: YES (iv) ANTI-SENSE: NO (xi) SEQUENCE DESCRIPTION: SEQ ID NO:26:

GGTGCTGGTC AGTTCCCACT GGGCGGTGTA GCGGCACGTC CGGGTTTCGG TCTGTCCCCG     60

ATCTTCCCAG GCGGTGCATG CCTGGGTAA     89

(2) INFORMATION FOR SEQ ID NO:27:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (iii) HYPOTHETICAL: YES (iv) ANTI-SENSE: NO (xi) SEQUENCE DESCRIPTION: SEQ ID NO:27:

AGCTTGCGGC CGTAAACGTA AATAATGATA G     31

(2) INFORMATION FOR SEQ ID NO:28:

(i) SEQUENCE CHARACTERISTICS:
        (A) LENGTH: 92 base pairs
        (B) TYPE: nucleic acid
        (C) STRANDEDNESS: single
        (D) TOPOLOGY: linear (iii) HYPOTHETICAL: YES (iv) ANTI-SENSE: YES (xi) SEQUENCE DESCRIPTION: SEQ ID NO:28:

GCGCACCACC GCCCAGTGCA CCCAGACCCG CGCCTGGGTA GAATACACCA CCCGGAACGC     60

CACCCGGGAT AGCACCCGGA ACGCCACCCA TG     92

(2) INFORMATION FOR SEQ ID NO:29:

(i) SEQUENCE CHARACTERISTICS:
        (A) LENGTH: 90 base pairs
        (B) TYPE: nucleic acid
        (C) STRANDEDNESS: single
        (D) TOPOLOGY: linear (iii) HYPOTHETICAL: YES (iv) ANTI-SENSE: YES (xi) SEQUENCE DESCRIPTION: SEQ ID NO:29:

TAACCGCCGG GAACGCGCCC AGACCTGCAC CCAGACCAGC ACCTGCCAGA CCGCCTGGAA     60

CCGGTTTCAG CGGTTTACCA CCCGGGCCCA     90

(2) INFORMATION FOR SEQ ID NO:30:

(i) SEQUENCE CHARACTERISTICS:
        (A) LENGTH: 86 base pairs
        (B) TYPE: nucleic acid
        (C) STRANDEDNESS: single
        (D) TOPOLOGY: linear (iii) HYPOTHETICAL: YES (iv) ANTI-SENSE: YES (xi) SEQUENCE DESCRIPTION: SEQ ID NO:30:

CCCGCCCAGA CCCGCACCTG CCTTTGCCGC TTTGTACGCA GCAGCTGCGT CTGCAACGCC    60

ACCCGGAACC AGAGCACCCG GGAAGG    86

(2) INFORMATION FOR SEQ ID NO:31:

(i) SEQUENCE CHARACTERISTICS:
        (A) LENGTH: 99 base pairs
        (B) TYPE: nucleic acid
        (C) STRANDEDNESS: single
        (D) TOPOLOGY: linear (iii) HYPOTHETICAL: YES (iv) ANTI-SENSE: YES (xi) SEQUENCE DESCRIPTION: SEQ ID NO:31:

CGGCAGACCA ACACCTGGAA CTTTGCCCGG TTTTACACCT GCACCCGGCT GCGGAACAAC    60

TGCGCCAGCA GATACACCCA GACCGCCAAC ACCTGGTAC    99

(2) INFORMATION FOR SEQ ID NO:32:

(i) SEQUENCE CHARACTERISTICS:
        (A) LENGTH: 99 base pairs
        (B) TYPE: nucleic acid
        (C) STRANDEDNESS: single
        (D) TOPOLOGY: linear (iii) HYPOTHETICAL: YES (iv) ANTI-SENSE: YES (xi) SEQUENCE DESCRIPTION: SEQ ID NO:32:

TGGTGCCTTC GGTTTAACAC CTGCACCGGT CGGAACGCCC GGCAGTACAC CAACACCTGG    60

GAAACGCGCG CCCGGCAGAA CACCACCCGG GTATACGCC    99

(2) INFORMATION FOR SEQ ID NO:33:

(i) SEQUENCE CHARACTERISTICS:
        (A) LENGTH: 98 base pairs
        (B) TYPE: nucleic acid
        (C) STRANDEDNESS: single
        (D) TOPOLOGY: linear (iii) HYPOTHETICAL: YES (iv) ANTI-SENSE: YES (xi) SEQUENCE DESCRIPTION: SEQ ID NO:33:

AGCTTCGGCG CTTTGATCGG GTAACCCAGC GGAACGCCTG GCTGCGGACC ACCGAACGGG    60

CCAACACCCG GGATACCCGC GAACGCGCCG CCTACACC    98

(2) INFORMATION FOR SEQ ID NO:34:

(i) SEQUENCE CHARACTERISTICS:
        (A) LENGTH: 90 base pairs
        (B) TYPE: nucleic acid
        (C) STRANDEDNESS: single
        (D) TOPOLOGY: linear (iii) HYPOTHETICAL: YES (iv) ANTI-SENSE: YES (xi) SEQUENCE DESCRIPTION: SEQ ID NO:34:

CCTGCTTTAC CCGCAGCACC TGCTACGCCA CCCGGACCGT AGCCGTACGG CAGTTTACCG    60

```
GTGGTGTACG GCAGACCGTA GCCACCTGGA                                          90

(2) INFORMATION FOR SEQ ID NO:35:

(i) SEQUENCE CHARACTERISTICS:
        (A) LENGTH: 90 base pairs
        (B) TYPE: nucleic acid
        (C) STRANDEDNESS: single
        (D) TOPOLOGY: linear (iii) HYPOTHETICAL: YES (iv) ANTI-SENSE: YES (xi) SEQUENCE DESCRIPTION: SEQ ID NO:35:

ACACCCGCTG CACCCGCGCC GAATTTTGCT GCTGCCTTCG CCGCAGCTGC CGCAGCAGCC         60

TGCGGACCAA CACCAGTACC GGTTGGGTAG                                          90

(2) INFORMATION FOR SEQ ID NO:36:

(i) SEQUENCE CHARACTERISTICS:
        (A) LENGTH: 91 base pairs
        (B) TYPE: nucleic acid
        (C) STRANDEDNESS: single
        (D) TOPOLOGY: linear (iii) HYPOTHETICAL: YES (iv) ANTI-SENSE: YES (xi) SEQUENCE DESCRIPTION: SEQ ID NO:36:

GGCCGCCGGA GTACCTACGC CTGCGATACC ACCGATGCCC GGGATCGCAC CTGGAACACC         60

CGGAACGCCA GCACCACCTA CGCCCGGCAG A                                        91

(2) INFORMATION FOR SEQ ID NO:37:

(i) SEQUENCE CHARACTERISTICS:
        (A) LENGTH: 75 base pairs
        (B) TYPE: nucleic acid
        (C) STRANDEDNESS: single
        (D) TOPOLOGY: linear (iii) HYPOTHETICAL: YES (iv) ANTI-SENSE: YES (xi) SEQUENCE DESCRIPTION: SEQ ID NO:37:

GCCTGGACCA CCCGGAACCA GGCCTGCTGC CGCACCGTAT TTAGCTGCTT TCGCCGCAGC         60

TGCCGCAGCC GCAGC                                                          75

(2) INFORMATION FOR SEQ ID NO:38:

(i) SEQUENCE CHARACTERISTICS:
        (A) LENGTH: 85 base pairs
        (B) TYPE: nucleic acid
        (C) STRANDEDNESS: single
        (D) TOPOLOGY: linear (iii) HYPOTHETICAL: YES (iv) ANTI-SENSE: YES (xi) SEQUENCE DESCRIPTION: SEQ ID NO:38:

CACCCGGTAC AACGGGATG CCCGCACCTG GAACACCTAC GCCCGGAACA CCAGCACCCG          60

GAACGCCTAC AACACCCGGA CCGAA                                               85
```

(2) INFORMATION FOR SEQ ID NO:39:

(i) SEQUENCE CHARACTERISTICS:
        (A) LENGTH: 82 base pairs
        (B) TYPE: nucleic acid
        (C) STRANDEDNESS: single
        (D) TOPOLOGY: linear (iii) HYPOTHETICAL: YES (iv) ANTI-SENSE: YES (xi) SEQUENCE DESCRIPTION: SEQ ID NO:39:

```
CCGTATTTCG CAGCTTTCGC AGCAGCCTTA GCTGCCGCTT CCGGGGATAC AACACCTGGA      60

ACCGCAGCGC CCGGGATACC TG                                               82
```

(2) INFORMATION FOR SEQ ID NO:40:

(i) SEQUENCE CHARACTERISTICS:
        (A) LENGTH: 90 base pairs
        (B) TYPE: nucleic acid
        (C) STRANDEDNESS: single
        (D) TOPOLOGY: linear (iii) HYPOTHETICAL: YES (iv) ANTI-SENSE: YES (xi) SEQUENCE DESCRIPTION: SEQ ID NO:40:

```
ATGCCACCAA CACCAACGCC GAAACCTGGG AAACCGCCTG CACCTACACC GTAGGTCGGG      60

ATGCCACCAA CACCAACGCC CGGACGAGCT                                       90
```

(2) INFORMATION FOR SEQ ID NO:41:

(i) SEQUENCE CHARACTERISTICS:
        (A) LENGTH: 90 base pairs
        (B) TYPE: nucleic acid
        (C) STRANDEDNESS: single
        (D) TOPOLOGY: linear (iii) HYPOTHETICAL: YES (iv) ANTI-SENSE: YES (xi) SEQUENCE DESCRIPTION: SEQ ID NO:41:

```
GCTGCCTGCG CTTCCGGGGA GATACCTACA CCTGGAACGC CACCAACACC CGGTACGCCA      60

CCAACAGACG GAACACCAGC TACACCCGGG                                       90
```

(2) INFORMATION FOR SEQ ID NO:42:

(i) SEQUENCE CHARACTERISTICS:
        (A) LENGTH: 89 base pairs
        (B) TYPE: nucleic acid
        (C) STRANDEDNESS: single
        (D) TOPOLOGY: linear (iii) HYPOTHETICAL: YES (iv) ANTI-SENSE: YES (xi) SEQUENCE DESCRIPTION: SEQ ID NO:42:

```
CTAGTCCGAA CTGCGCTGCT TTAGCCGCTG CTTTAGCAGC TGCTGCCGCC GGAGTACCAA      60

CGCCGTACTT CGCTGCTTTA GCTGCCGCA                                        89
```

(2) INFORMATION FOR SEQ ID NO:43:

(i) SEQUENCE CHARACTERISTICS:
            (A) LENGTH: 96 base pairs
            (B) TYPE: nucleic acid
            (C) STRANDEDNESS: single
            (D) TOPOLOGY: linear (iii) HYPOTHETICAL: YES (iv) ANTI-SENSE: YES (xi) SEQUENCE DESCRIPTION: SEQ ID NO:43:

CTGGTGCAAC GCCAACACCC GGTGCCAGAC CTACGCCCGG AGCAACACCA ACACCCGGTG        60

CTACGCCAAC ACCTGGCGCA ACACCTACGC CCGGAA                                 96

(2) INFORMATION FOR SEQ ID NO:44:

(i) SEQUENCE CHARACTERISTICS:
            (A) LENGTH: 95 base pairs
            (B) TYPE: nucleic acid
            (C) STRANDEDNESS: single
            (D) TOPOLOGY: linear (iii) HYPOTHETICAL: YES (iv) ANTI-SENSE: YES (xi) SEQUENCE DESCRIPTION: SEQ ID NO:44:

TTTCGCAGCA ACCTTCGCAG CAGATTTCGC AGCAGCCGCA ACGCCACCCG GACCGATACC        60

CGGTGCTACA CCAACGCCCG GCGCAACACC TACAC                                  95

(2) INFORMATION FOR SEQ ID NO:45:

(i) SEQUENCE CHARACTERISTICS:
            (A) LENGTH: 90 base pairs
            (B) TYPE: nucleic acid
            (C) STRANDEDNESS: single
            (D) TOPOLOGY: linear (iii) HYPOTHETICAL: YES (iv) ANTI-SENSE: YES (xi) SEQUENCE DESCRIPTION: SEQ ID NO:45:

CCCTGCACCT ACACCCAGGC CCGGAACACC AACACCTACA CCCAGACCTG GGATGCCCGC        60

ACCCAGACCA GCTGCTGCAC GCAGCTGCGC                                        90

(2) INFORMATION FOR SEQ ID NO:46:

(i) SEQUENCE CHARACTERISTICS:
            (A) LENGTH: 96 base pairs
            (B) TYPE: nucleic acid
            (C) STRANDEDNESS: single
            (D) TOPOLOGY: linear (iii) HYPOTHETICAL: YES (iv) ANTI-SENSE: YES (xi) SEQUENCE DESCRIPTION: SEQ ID NO:46:

ACCTTCACGC AGTTCTGGAG ACAGGGAACG ACGTACACCT TCGTCCGCGC CAGCACCGAA        60

ACCCGGAACG CCTGCACCAA CACCCAGGCC CGGTAC                                 96

(2) INFORMATION FOR SEQ ID NO:47:

(i) SEQUENCE CHARACTERISTICS:
            (A) LENGTH: 81 base pairs
            (B) TYPE: nucleic acid (C) STRANDEDNESS: single
        (D) TOPOLOGY: linear (iii) HYPOTHETICAL: YES (iv) ANTI-SENSE: YES (xi) SEQUENCE DESCRIPTION: SEQ ID NO:47:

CGCCGCTTTC GCAGCAGCCA GCGCGCCCGG AACACGTGGA GAGGACGGGG TAGACGGCAG      60

GTGCTGGGAA GAGGACGGGT C      81

(2) INFORMATION FOR SEQ ID NO:48:

(i) SEQUENCE CHARACTERISTICS:
        (A) LENGTH: 92 base pairs
        (B) TYPE: nucleic acid
        (C) STRANDEDNESS: single
        (D) TOPOLOGY: linear (iii) HYPOTHETICAL: YES (iv) ANTI-SENSE: YES (xi) SEQUENCE DESCRIPTION: SEQ ID NO:48:

GCTGGGCCTG CACCTACAAC ACCGCCCGGG ATACCAACAC CGCCCAGAGC ACCCAGACCG      60

CCCAGTACAC CCGGAACCGC TGCACCGTAT TT      92

(2) INFORMATION FOR SEQ ID NO:49:

(i) SEQUENCE CHARACTERISTICS:
        (A) LENGTH: 98 base pairs
        (B) TYPE: nucleic acid
        (C) STRANDEDNESS: single
        (D) TOPOLOGY: linear (iii) HYPOTHETICAL: YES (iv) ANTI-SENSE: YES (xi) SEQUENCE DESCRIPTION: SEQ ID NO:49:

CACCCAGACC GCCAACACCC AGACCGCCCA GACCTGCTGC ACCAACCAGA CCGAACTGAG      60

CTGCTTTCGC CGCTGCCTTT GCCGCAGCAG CAGCTGCA      98

(2) INFORMATION FOR SEQ ID NO:50:

(i) SEQUENCE CHARACTERISTICS:
        (A) LENGTH: 86 base pairs
        (B) TYPE: nucleic acid
        (C) STRANDEDNESS: single
        (D) TOPOLOGY: linear (iii) HYPOTHETICAL: YES (iv) ANTI-SENSE: YES (xi) SEQUENCE DESCRIPTION: SEQ ID NO:50:

AACGCCACCC AGACCTGCTG CACCGTATTT AGCCGCTTTA GCTGCCGCCG CCGGCGGGAT      60

GCCACCCAGA CCACCAACGC CCGGTA      86

(2) INFORMATION FOR SEQ ID NO:51:

(i) SEQUENCE CHARACTERISTICS:
        (A) LENGTH: 99 base pairs
        (B) TYPE: nucleic acid
        (C) STRANDEDNESS: single
        (D) TOPOLOGY: linear (iii) HYPOTHETICAL: YES (iv) ANTI-SENSE: YES (xi) SEQUENCE DESCRIPTION: SEQ ID NO:51:

| AGCTTTACCC AGGCATGCAC CGCCTGGGAA GATCGGGGAC AGACCGAAAC CCGGACGTGC | 60 |
| CGCTACACCG CCCAGTGGGA ACTGACCAGC ACCACCCAG | 99 |

(2) INFORMATION FOR SEQ ID NO:52:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (iii) HYPOTHETICAL: YES (iv) ANTI-SENSE: YES (xi) SEQUENCE DESCRIPTION: SEQ ID NO:52:

| GATCCTATCA TTATTTACGT TTACGGCCGC A | 31 |

(2) INFORMATION FOR SEQ ID NO:53:

(i) SEQUENCE CHARACTERISTICS:
        (A) LENGTH: 2210 base pairs
        (B) TYPE: nucleic acid
        (C) STRANDEDNESS: double
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:53:

| GATCCATGGG AGGGGTCCCT GGGGCCATTC CTGGTGGAGT TCCTGGAGGA GTCTTTTATC | 60 |
| CAGGGGCTGG TCTCGGAGCC CTTGGAGGAG GAGCGCTGGG GCCTGGAGGC AAACCTCTTA | 120 |
| AGCCAGTTCC CGGAGGGCTT GCGGGTGCTG GCCTTGGGGC AGGGCTCGGC GCCTTCCCCG | 180 |
| CAGTTACCTT TCCGGGGGCT CTGGTGCCTG GTGGAGTGGC TGACGCTGCT GCAGCCTATA | 240 |
| AAGCTGCTAA GGCTGGCGCT GGGCTTGGTG GTGTCCCAGG AGTTGGTGGC TTAGGAGTGT | 300 |
| CTGCAGGTGC GGTGGTTCCT CAGCCTGGAG CCGGAGTGAA GCCTGGGAAA GTGCCGGGTG | 360 |
| TGGGGCTGCC AGGTGTATAC CCAGGTGGCG TGCTCCCAGG AGCTCGGTTC CCCGGTGTGG | 420 |
| GGGTGCTCCC TGGAGTTCCC ACTGGAGCAG GAGTTAAGCC CAAGGCTCCA GGTGTAGGTG | 480 |
| GAGCTTTTGC TGGAATCCCA GGAGTTGGAC CCTTTGGGGG ACCGCAACCT GGAGTCCCAC | 540 |
| TGGGGTATCC CATCAAGGCC CCAAGCTGC CTGGTGGCTA TGGACTGCCC TACACCACAG | 600 |
| GGAAACTGCC CTATGGCTAT GGGCCCGGAG GAGTGGCTGG TGCAGCGGGC AAGGCTGGTT | 660 |
| ACCCAACAGG GACAGGGGTT GGCCCCCAGG CAGCAGCAGC AGCGGCAGCT AAAGCAGCAG | 720 |
| CAAAGTTCGG TGCTGGAGCA GCCGGAGTCC TCCCTGGTGT TGGAGGGGCT GGTGTTCCTG | 780 |
| GCGTGCCTGG GGCAATTCCT GGAATTGGAG GCATCGCAGG CGTTGGGACT CCAGCTGCAG | 840 |
| CTGCAGCTGC AGCAGCAGCC GCTAAGGCAG CCAAGTATGG AGCTGCTGCA GGCTTAGTGC | 900 |
| CTGGTGGGCC AGGCTTTGGC CCGGGAGTAG TTGGTGTCCC AGGAGCTGGC GTTCAGGTG | 960 |
| TTGGTGTCCC AGGAGCTGGG ATTCCAGTTG TCCCAGGTGC TGGGATCCCA GGTGCTGCGG | 1020 |
| TTCCAGGGGT TGTGTCACCA GAAGCAGCTG CTAAGGCAGC TGCAAAGGCA GCCAAATACG | 1080 |

-continued

```
GGGCCAGGCC CGGAGTCGGA GTTGGAGGCA TTCCTACTTA CGGGGTTGGA GCTGGGGGCT      1140

TTCCCGGCTT TGGTGTCGGA GTCGGAGGTA TCCCTGGAGT CGCAGGTGTC CCTAGTGTCG      1200

GAGGTGTTCC CGGAGTCGGA GGTGTCCCGG GAGTTGGCAT TTCCCCCGAA GCTCAGGCAG      1260

CAGCTGCCGC CAAGGCTGCC AAGTACGGAG TGGGGACCCC AGCAGCTGCA GCTGCTAAAG      1320

CAGCCGCCAA AGCCGCCCAG TTTGGGTTAG TTCCTGGTGT CGGCGTGGCT CCTGGAGTTG      1380

GCGTGGCTCC TGGTGTCGGT GTGGCTCCTG GAGTTGGCTT GGCTCCTGGA GTTGGCGTGG      1440

CTCCTGGAGT TGGTGTGGCT CCTGGCGTTG GCGTGGCTCC CGGCATTGGC CCTGGTGGAG      1500

TTGCAGCTGC AGCAAAATCC GCTGCCAAGG TGGCTGCCAA AGCCCAGCTC CGAGCTGCAG      1560

CTGGGCTTGG TGCTGGCATC CCTGGACTTG GAGTTGGTGT CGGCGTCCCT GGACTTGGAG      1620

TTGGTGCTGG TGTTCCTGGA CTTGGAGTTG GTGCTGGTGT TCCTGGCTTC GGGGCAGGTG      1680

CAGATGAGGG AGTTAGGCGG AGCCTGTCCC CTGAGCTCAG GGAAGGAGAT CCCTCCTCCT      1740

CTCAGCACCT CCCCAGCACC CCCTCATCAC CCAGGGTACC TGGAGCCCTG GCTGCCGCTA      1800

AAGCAGCCAA ATATGGAGCA GCAGTGCCTG GGGTCCTTGG AGGGCTCGGG GCTCTCGGTG      1860

GAGTAGGCAT CCCAGGCGGT GTGGTGGGAG CCGGACCCGC CGCCGCCGCT GCCGCAGCCA      1920

AAGCTGCTGC CAAAGCCGCC CAGTTTGGCC TAGTGGGAGC CGCTGGGCTC GGAGGACTCG      1980

GAGTCGGAGG GCTTGGAGTT CCAGGTGTTG GGGGCCTTGG AGGTATACCT CCAGCTGCAG      2040

CCGCTAAAGC AGCTAAATAC GGTGCTGCTG GCCTTGGAGG TGTCCTAGGG GGTGCCGGGC      2100

AGTTCCCACT TGGAGGAGTG GCAGCAAGAC CTGGCTTCGG ATTGTCTCCC ATTTTCCCAG      2160

GTGGGGCCTG CCTGGGGAAA GCTTGTGGCC GGAAGAGAAA ATGATGATAG                2210
```

(2) INFORMATION FOR SEQ ID NO:54:

(i) SEQUENCE CHARACTERISTICS:
        (A) LENGTH: 4045 base pairs
        (B) TYPE: nucleic acid
        (C) STRANDEDNESS: double
        (D) TOPOLOGY: circular (ii) MOLECULE TYPE: DNA (genomic)

(iii) HYPOTHETICAL: NO (iv) ANTI-SENSE: NO (xi) SEQUENCE DESCRIPTION: SEQ ID NO:54:

```
TTCACTGGCC GTCGTTTTAC AACGTCGTGA CTGGGAAAAC CCTGGCGTTA CCCAACTTAA        60

TCGCCTTGCA GCACATCCCC CTTTCGCCAG CTGGCGTAAT AGCGAAGAGG CCCGCACCGA       120

TCGCCCTTCC CAACAGTTGC GCAGCCTGAA TGGCGAATGG CGCCTGATGC GGTATTTTCT       180

CCTTACGCAT CTGTGCGGTA TTTCACACCG CATATGGTGC ACTCTCAGTA CAATCTGCTC       240

TGATGCCGCA TAGTTAAGCC AGCCCCGACA CCCGCCAACA CCCGCTGACG CGCCCTGACG       300

GGCTTGTCTG CTCCCGGCAT CCGCTTACAG ACAAGCTGTG ACCGTCTCCG GGAGCTGCAT       360

GTGTCAGAGG TTTTCACCGT CATCACCGAA ACGCGCGAGA CGAAAGGGCC TCGTGATACG       420

CCTATTTTTA TAGGTTAATG TCATGATAAT AATGGTTTCT TAGACGTCAG GTGGCACTTT       480

TCGGGGAAAT GTGCGCGGAA CCCCTATTTG TTTATTTTTC TAAATACATT CAAATATGTA       540

TCCGCTCATG AGACAATAAC CCTGATAAAT GCTTCAATAA TATTGAAAAA GGAAGAGTAT       600

GAGTATTCAA CATTTCCGTG TCGCCCTTAT TCCCTTTTTT GCGGCATTTT GCCTTCCTGT       660

TTTTGCTCAC CCAGAAACGC TGGTGAAAGT AAAAGATGCT GAAGATCAGT TGGGTGCACG       720
```

| | |
|---|---|
| AGTGGGTTAC ATCGAACTGG ATCTCAACAG CGGTAAGATC CTTGAGAGTT TTCGCCCCGA | 780 |
| AGAACGTTTT CCAATGATGA GCACTTTTAA AGTTCTGCTA TGTGGCGCGG TATTATCCCG | 840 |
| TATTGACGCC GGGCAAGAGC AACTCGGTCG CCGCATACAC TATTCTCAGA ATGACTTGGT | 900 |
| TGAGTACTCA CCAGTCACAG AAAAGCATCT TACGGATGGC ATGACAGTAA GAGAATTATG | 960 |
| CAGTGCTGCC ATAACCATGA GTGATAACAC TGCGGCCAAC TTACTTCTGA CAACGATCGG | 1020 |
| AGGACCGAAG GAGCTAACCG CTTTTTTGCA CAACATGGGG GATCATGTAA CTCGCCTTGA | 1080 |
| TCGTTGGGAA CCGGAGCTGA ATGAAGCCAT ACCAAACGAC GAGCGTGACA CCACGATGCC | 1140 |
| TGTAGCAATG GCAACAACGT TGCGCAAACT ATTAACTGGC GAACTACTTA CTCTAGCTTC | 1200 |
| CCGGCAACAA TTAATAGACT GGATGGAGGC GGATAAAGTT GCAGGACCAC TTCTGCGCTC | 1260 |
| GGCCCTTCCG GCTGGCTGGT TTATTGCTGA TAAATCTGGA GCCGGTGAGC GTGGGTCTCG | 1320 |
| CGGTATCATT GCAGCACTGG GGCCAGATGG TAAGCCCTCC CGTATCGTAG TTATCTACAC | 1380 |
| GACGGGGAGT CAGGCAACTA TGGATGAACG AAATAGACAG ATCGCTGAGA TAGGTGCCTC | 1440 |
| ACTGATTAAG CATTGGTAAC TGTCAGACCA AGTTTACTCA TATATACTTT AGATTGATTT | 1500 |
| AAAACTTCAT TTTTAATTTA AAAGGATCTA GGTGAAGATC CTTTTTGATA ATCTCATGAC | 1560 |
| CAAAATCCCT TAACGTGAGT TTTCGTTCCA CTGAGCGTCA GACCCCGTAG AAAAGATCAA | 1620 |
| AGGATCTTCT TGAGATCCTT TTTTTCTGCG CGTAATCTGC TGCTTGCAAA CAAAAAAACC | 1680 |
| ACCGCTACCA GCGGTGGTTT GTTTGCCGGA TCAAGAGCTA CCAACTCTTT TTCCGAAGGT | 1740 |
| AACTGGCTTC AGCAGAGCGC AGATACCAAA TACTGTTCTT CTAGTGTAGC CGTAGTTAGG | 1800 |
| CCACCACTTC AAGAACTCTG TAGCACCGCC TACATACCTC GCTCTGCTAA TCCTGTTACC | 1860 |
| AGTGGCTGCT GCCAGTGGCG ATAAGTCGTG TCTTACCGGG TTGGACTCAA GACGATAGTT | 1920 |
| ACCGGATAAG CGCAGCGGT CGGGCTGAAC GGGGGGTTCG TGCACACAGC CCAGCTTGGA | 1980 |
| GCGAACGACC TACACCGAAC TGAGATACCT ACAGCGTGAG CATTGAGAAA GCGCCACGCT | 2040 |
| TCCCGAAGGG AGAAAGGCGG ACAGGTATCC GGTAAGCGGC AGGGTCGGAA CAGGAGAGCG | 2100 |
| CACGAGGGAG CTTCCAGGGG GAAACGCCTG GTATCTTTAT AGTCCTGTCG GGTTTCGCCA | 2160 |
| CCTCTGACTT GAGCGTCGAT TTTTGTGATG CTCGTCAGGG GGGCGGAGCC TATGGAAAAA | 2220 |
| CGCCAGCAAC GCGGCCTTTT TACGGTTCCT GGCCTTTTGC TGGCCTTTTG CTCACATGTT | 2280 |
| CTTTCCTGCG TTATCCCCTG ATTCTGTGGA TAACCGTATT ACCGCCTTTG AGTGAGCTGA | 2340 |
| TACCGCTCGC CGCAGCCGAA CGACCGAGCG CAGCGAGTCA GTGAGCGAGG AAGCGGAAGA | 2400 |
| GCGCCCAATA CGCAAACCGC CTCTCCCCGC GCGTTGGCCG ATTCATTAAT GCAGCTGGCA | 2460 |
| CGACAGGTTT CCCGACTGGA AAGCGGGCAG TGAGCGCAAC GCAATTAATG TGAGTTAGCT | 2520 |
| CACTCATTAG GCACCCCAGG CTTTACACTT TATGCTTCCG GCTCGTATGT TGTGTGGAAT | 2580 |
| TGTGAGCGGA TAACAATTTC ACACAGGAAA CAGCTATGAC CATGATTACG CCAAGCTTGG | 2640 |
| CTGCAGGTGA TGATTATCAG CCAGCAGAGA TTAAGGAAAA CAGACAGGTT TATTGAGCGC | 2700 |
| TTATCTTTCC CTTTATTTTT GCTGCGGTAA GTCGCATAAA AACCATTCTT CATAATTCAA | 2760 |
| TCCATTTACT ATGTTATGTT CTGAGGGGAG TGAAAATTCC CCTAATTCGA TGAAGATTCT | 2820 |
| TGCTCAATTG TTATCAGCTA TGCGCCGACC AGAACACCTT GCCGATCAGC CAAACGTCTC | 2880 |
| TTCAGGCCAC TGACTAGCGA TAACTTTCCC CACAACGGAA CAACTCTCAT GCATGGGAT | 2940 |
| CATTGGGTAC TGTGGGTTTA GTGGTTGTAA AAACACCTGA CCGCTATCCC TGATCAGTTT | 3000 |
| CTTGAAGGTA AACTCATCAC CCCCAAGTCT GGCTATGCAG AAATCACCTG GCTCAACAGC | 3060 |

-continued

| | | | | |
|---|---|---|---|---|
| CTGCTCAGGG | TCAACGAGAA | TTAACATTCC | GTCAGGAAAG | CTTGGCTTGG AGCCTGTTGG 3120 |
| TGCGGTCATG | GAATTACCTT | CAACCTCAAG | CCAGAATGCA | GAATCACTGG CTTTTTTGGT 3180 |
| TGTGCTTACC | CATCTCTCCG | CATCACCTTT | GGTAAAGGTT | CTAAGCTTAG GTGAGAACAT 3240 |
| CCCTGCCTGA | ACATGAGAAA | AAACAGGGTA | CTCATACTCA | CTTCTAAGTG ACGGCTGCAT 3300 |
| ACTAACCGCT | TCATACATCT | CGTAGATTTC | TCTGGCGATT | GAAGGGCTAA ATTCTTCAAC 3360 |
| GCTAACTTTG | AGAATTTTTG | CAAGCAATGC | GGCGTTATAA | GCATTTAATG CATTGATGCC 3420 |
| ATTAAATAAA | GCACCAACGC | CTGACTGCCC | CATCCCCATC | TTGTCTGCGA CAGATTCCTG 3480 |
| GGATAAGCCA | AGTTCATTTT | TCTTTTTTTC | ATAAATTGCT | TTAAGGCGAC GTGCGTCCTC 3540 |
| AAGCTGCTCT | TGTGTTAATG | GTTTCTTTTT | TGTGCTCATA | CGTTAAATCT ATCACCGCAA 3600 |
| GGGATAAATA | TCTAACACCG | TGCGTGTTGA | CTATTTTACC | TCTGGCGGTG ATAATGGTTG 3660 |
| CATGTACTAA | GGAGGTTGTA | TGGAACAACG | CATAACCCTG | AAAGATTATG CAATGCGCTT 3720 |
| TGGGCAAACC | AAGACAGCTA | AAGATCTCTC | ACCTACCAAA | CAATGCCCCC CTGCAAAAAA 3780 |
| TAAATTCATA | TAAAAAACAT | ACAGATAACC | ATCTGCGGTG | ATAAATTATC TCTGGCGGTG 3840 |
| TTGACATAAA | TACCACTGGC | GGTGATACTG | AGCACATCAG | CAGGACGCAC TGACCACCAT 3900 |
| GAAGGTGACG | CTCTTAAAAA | TTAAGCCCTG | AAGAAGGGCA | GCATTCAAAG CAGAAGGCTT 3960 |
| TGGGGTGTGT | GATACGAAAC | GAAGCATTGG | GATCCTAAGG | AGGTTTAAGA TCCATGGGTT 4020 |
| TAAACCTCCT | TAGGATCCCC | GGGAA | | 4045 |

SYNTHETIC POLYNUCLEOTIDES ENCODING TROPOELASTIN

This application is a 371 of PCT/AU93/00655, filed Dec. 16, 1993.

TECHNICAL FIELD

The present invention relates to the production of recombinant tropoelastins, and variants of these recombinant tropoelastins, from synthetic polynucleotides, and uses of the tropoelastins and variants.

BACKGROUND ART

There are various forms of tropoelastin that typically appear to consist of two types of alternating domains: those rich in hydrophobic amino acids (responsible for the elastic properties) and those rich in lysin residues (responsible for cross-link formation). Hydrophobic and cross-linking domains are encoded in separate exons (Indik et al. 1987).

The gene for tropoelastin is believed to be present as a single copy in the mammalian genome, and is expressed in the form of multiple transcripts, distinguished by alternative splicing of the pre-mRNA (Indik et al, 1990; Oliver et al, 1987).

Previous recombinant work with tropoelastin has been reported by Indik et al (1990) who achieved modest expression of a natural human tropoelastin sequence from cDNA. Their product was unstable, the free polypeptide being rapidly degraded.

Bressan et al (1987) have reported the cloning of a defined naturally occurring segment of chick tropoelastin.

DESCRIPTION OF THE INVENTION

The present invention provides for the expression of significant amounts of tropoelastins or variants of the tropoelastins in recombinant expression systems.

The present inventors have recognised that tropoelastins are proteins which can be used in a variety of, for instance, pharmaceutical applications, but these uses require significant quantities of tropoelastin. These quantities could be obtained by cloning naturally occurring tropoelastin genes, but the present inventors show how they can be more easily obtained by producing synthetic polynucleotides adapted to provide enhanced expression.

The present inventors have recognised that because tropoelastins have highly repetitive coding sequences, the tropoelastin genes have the potential to include significant numbers of codons which have low usage in particular hosts. Codons of low usage can hamper gene expression.

For example, in one tropoelastin coding sequence described in detail in this application, the natural sequence contains of the order of 80 glycine GGA codons which comprises 10% of the gene and have low usage in *Escherichia coli* [Fazio et al., 1988, and Genetics Computer Group (GCG) package version 7-UNIX using Codon Frequency and Gen Run Data: ecohigh-cod].

According to a first aspect of the present invention, there is provided a synthetic polynucleotide encoding the amino acid sequence of a tropoelastin or a variant of the tropoelastin.

The tropoelastin may be a mammalian or avian tropoelastin such as human, bovine, ovine, porcine, rat or chick tropoelastin. Preferably, the tropoelastin is human tropoelastin.

The synthetic polynucleotide sequence is altered with respect to the natural coding sequence for the tropoelastin molecule or variant so that:

a) it codes for a tropoelastin sequence or a variant of the tropoelastin; and
b) all or some of the codons which hamper expression in the expression system in which the polynucleotide is to be expressed, are replaced with codons more favourable for expression in the expression system.

Preferably all, or part, of the 5' or 3' untranslated regions, or both, of the natural coding sequence are excluded from the synthetic polynucleotide.

Preferably all, or part, of the signal peptide encoding region is excluded from the synthetic polynucleotide.

Where the synthetic polynucleotide is prepared from assembled oligonucleotides it is preferred to incorporate restriction sites in the sequence to facilitate assembly of the polynucleotide.

Restriction sites incorporated in the polynucleotide sequence are also useful for:

1. facilitating subcloning of manageable blocks for sequence confirmation;
2. providing sites for later introduction of modifications to the polynucleotide as insertions, deletions or base changes;
3. facilitating confirmation of correct polynucleotide assembly by restriction endonuclease digestion.

A preferred expression system is an *Escherichia coli* expression system. However, the invention includes within its scope synthetic polynucleotides suitable for use in other expression systems such as other microbial expression systems. These other expression systems include yeast and bacterial expression systems, insect cell expression systems, and expression systems involving other eukaryotic cell lines or whole organisms.

Modifications to codon usage to provide enhanced expression are discussed in:

Zhang et al (1991) for *E. coli*, yeast, fruit fly and primates where codon usage tables are provided;

Newgard et al (1986) for mammals; and Murray et al (1989) for plants. Preferred codon usages are indicated in these publications.

Preferably, at least 50% of codons for any particular amino acid are selected and altered to reflect preferred codon usage in the host of choice.

Preferably, the polynucleotide is a fused polynucleotide with the tropoelastin or variant encoding sequence fused to a polynucleotide sequence compatible with the host. The compatible sequence is preferably at the 5' end of the polynucleotide molecule.

Preferred compatible polynucleotides include those which encode all or part of a polypeptide which causes the expressed fusion to be secreted or expressed as a cell surface protein so as to facilitate purification of the expressed product, or expressed as a cytoplasmic protein.

One preferred compatible polynucleotide is one encoding all or part of glutathione-S-transferase.

In addition the synthetic polynucleotides can encode additional residues such as an N-terminal methionine or f-methionine not present in the natural counterpart.

A preferred synthetic polynucleotide is one comprising the sequence illustrated in FIGS. 3 (1) to 3 (5) (SEQ ID NO 1) or a part of it, encoding a polypeptide which retains elastic properties. The sequence illustrated in FIGS. 3 (1) to 3 (5) is 2210 bp in size.

To our knowledge, this is the largest synthetic gene constructed so fat. Previously, the largest was of the order of 1.5 kb in size.

The actual changes made in this sequence in comparison with the natural sequence from which it was derived are shown in FIGS. 6 (1) to 6 (4) comparing the synthetic sequence (SEQ ID NO 1) with the natural sequence (SEQ ID NO 53). Synthetic polynucleotides in which only some of the base changes shown in that Figure have been made are also within the scope of the invention.

It is known that tropoelastin genes in nature are expressed as multiple transcripts which are distinguished by alternative splicing of the pre-mRNA as described in, for instance:

Indik et al, 1990; Oliver et al, 1987; Heim et al, 1991; Raju et al, 1987; and Yeh et al, 1987. The tropoelastins of the present invention for which synthetic polynucleotides are prepared are intended to encompass these different splice forms.

Variants of tropoelastins embodying the present invention are polypeptides which retain the basic structural attributes, namely the elastic properties, of a tropoelastin molecule, and which are homologous to naturally occurring tropoelastin molecules. For the purposes of this description, "homology" between two sequences connotes a likeness short of identity indicative of a derivation of one sequence from the other. In particular, a polypeptide is homologous to a tropoelastin molecule if a comparison of amino-acid sequences between the molecules reveals an identity of greater than about 65% over any contiguous 20 amino acid stretch or over any repetitive element of the tropoelastin molecule shorter than 20 amino acids in length. Such a sequence comparison can be performed via known algorithms, such as the one described by Lipman and Pearson, Science 227: 1435 (1985) which are readily implemented by computer.

Variants of tropoelastins can be produced by conventional site-directed or random mutagenesis. This is one avenue for routinely identifying residues of the molecule that can be modified without destroying the elastic properties of the molecule.

Oligonucleotide-directed mutagenesis, comprising:
1. synthesis of an oligonucleotide with a sequence that contains the desired nucleotide substitution (mutation),
2. hybridizing the oligonucleotide to a template comprising a structural sequence coding for tropoelastin and
3. using DNA polymerase to extend the oligonucleotide as a primer, is preferred because of its ready utility in determining the effects of particular changes to the structural sequence. Its relative expense may militate in favour of an alternative, known direct or random mutagenesis method.

Another approach which is particularly suited to situations where the synthetic polynucleotide has been prepared from oligonucleotide blocks bounded by restrictions sites is cassette mutagenesis where entire restriction fragments are inserted, deleted or replaced.

Also exemplary of variants within the present invention are molecules that correspond to a portion of a tropoelastin molecule without being coincident with a natural tropoelastin molecule and which retain the elastic properties of a natural tropoelastin molecule.

Other variants of tropoelastins of the present invention are fragments that retain the elastic properties of a tropoelastin molecule.

Fragments within the scope of this invention are typically greater than 20 amino acids in length.

According to a second aspect of the present invention there is provided a recombinant DNA molecule comprising a synthetic polynucleotide of the first aspect, and vector DNA.

Vectors useful in the invention include plasmids, phages and phagemids. The synthetic polynucleotides of the present invention can also be used in integrative expression systems or lytic or comparable expression systems.

Suitable vectors will generally contain origins of replication and control sequences which are derived from species compatible with the intended expression host. Typically these vectors include a promoter located upstream from the synthetic polynucleotide, together with a ribosome binding site for prokaryotic expression, and a phenotypic selection gene such as one conferring antibiotic resistance or supplying an auxotrophic requirement. For production vectors, vectors which provide for enhanced stability through partitioning may be chosen. Where integrative vectors are used it is not necessary for the vector to have an origin of replication. Lytic and other comparable expression systems do not need to have those functions required for maintenance of vectors in hosts.

Typical vectors include pBR322, pBluescript II SK[30], pGEX-2T, pTrc99A, pET series vectors, particularly pET3d, (Studier et al; 1990) and derivatives of these vectors.

According to a third aspect of the present invention there is provided a transformed host transformed with a recombinant DNA molecule of the second aspect.

Hosts embodying the invention include bacteria, yeasts, insect cells and other eukaryotic cells or whole organisms. They are typically bacterial hosts.

A preferred host is an *E. coli* strain. Example of *E. coli* hosts include *E. coli* B strain derivatives (Studier et al, 1990), NM522 (Gough and Murray, 1983) and XL-1-Blue (Bullock et al, 1987). Hosts embodying this invention, for providing enhanced expression of tropoelastin or tropoelastin variants, are those in which the altered codon usage is favourable for expression, and with which any control sequences present in the recombinant DNA are compatible.

According to a fourth aspect of the present invention there is provided an expression product of a transformed host of the third aspect which expression product comprises a tropoelastin or a variant thereof.

A preferred expression produce of the fourth aspect comprises all or part of the amino-acid sequence depicted in FIGS. 3 (1) to 3 (5) (SEQ ID NO: 1). The serine at position 1 may be deleted from the product and similarly the methionine at position 2 may be deleted.

Other preferred expression products are those in which only some of the base changes shown in FIGS. 6 (1) to 6 (4) have been made. Typically at least 50% of the indicated base changes have been made.

The expression products of the fourth aspect may be fused expression products which include all or part of a protein encoded by the vector in peptide linkage with the expression product. They may also include, for example, an N-terminal methionine or other additional residues which do not impair the elastic properties of the product.

Typically the fusion is to the N-terminus of the expression product. An example of a suitable protein is glutathione-S-transferase. The fused protein sequence may be chosen in order to cause the expression product to be secreted or expressed as a cell surface protein to simplify purification or expressed as a cytoplasmic protein.

The expressed fusion products may subsequently be treated to remove the fused protein sequences to provide free tropoelastin or a free tropoelastin variant.

The expression products of the fourth aspect may also be produced from non-fusion vectors such as pND211 (N. Dixon, Australian National University). This vector has the gene inserted into an NcoI site and uses lambda-promoter-driven expression to permit initiation from the start codon of the synthetic gene. The sequence of the vector is shown at FIGS. 9 (1) and 9 (2) (SEQ ID NO: 54). Other suitable non-fusion vectors include pET3d.

According to a fifth aspect of the present invention there is provided a pharmaceutical or veterinary composition comprising an expression product of the fourth aspect together with a pharmaceutically or veterinarally acceptable carrier.

Dosage of the expression product and choice of carrier will vary with the specific purpose for which the expression product is being administered.

The expression products of the fourth aspect may also be prepared in the form of foods or as industrial products where elastic or association properties may be desired. The tropoelastin expression products of the invention can form associations in solution wherein the tropoelastin molecules are held together by hydrophobic interactions. These associations are termed "coacervates". They are useful as precursors to elastin synthesis. The tropoelastin coacervates can also be used as delivery vehicles for active ingredients such as pharmaceutical or veterinary agents providing biodegradable or biodissociable slow release formulations or alternatively protective coatings to protect active agents, for instance, during their transit through the stomach of a host.

According to a sixth aspect of the present invention there is provided a process for the production of an expression product of the fourth aspect comprising:

providing a transformed host of the third aspect; culturing it under conditions suitable for the expression of the product of the fourth aspect; and collecting the expression product.

In one preferred form the expression product is produced in the form of inclusion bodies which are harvested from the transformed host.

In a seventh aspect of the invention there is provided a cross-linked expression product of the fourth aspect. The cross-linked expression products form elastin or elastin-like products.

In preparing a synthetic polynucleotide in accordance with the first aspect the following procedure is followed.

A cDNA sequence encoding a tropoelastin, or a part of it, is selected and the open reading frame is defined.

The sequence is then translated to provide the corresponding amino acid sequence. Alternatively, the procedure can commence from a known amino acid sequence.

The exons which are to be included in the expression product are chosen. Preferably, any signal sequence or untranslated regions will not be included in the synthetic polynucleotide.

The amino acid sequence selected is then converted to a polynucleotide sequence on the basis of codon usage frequencies. By selecting the most commonly used codon for each amino acid for the host in which expression is desired, a skewed usage arises because particular codons may have very different frequencies of usage. It is therefore necessary to adjust the codon usage of at least the most common codons, that is, those present at greater than 20 occurrences, to more closely match levels of codon usage in the host of choice.

It is preferably to alter the sequence to introduce restriction sites at regular intervals throughout the sequence where these represent silent alterations, that is, they do not change the resulting amino acid. In addition ends suitable for ligation, eg BamHI and/or NcoI sites can be introduced into the sequence.

Tropoelastin sequences described for various organisms are similar, particularly at the level of exon structure and the organisation of hydrophilic and hydrophobic domains. In selecting exons to be included in the expression product we have adopted an approach whereby we leave in exons known to occur in all available tropoelastins. Depending on the intended use of the resulting tropoelastin, additional exons, or synthetic sequences, or both, are included. For instance, in the human example provided we included exon 10A which only occurs in some of the know sequences for human tropoelastin. In the bovine case, a typical addition would be exons 4A, 6 and/or 9 (Raju and Anwar, 1987; Yeh et al, 1987). In the rat case, a typical addition would be exons corresponding to exons 12 through 15 of the bovine case. (Heim et al 1991).

The construction of the synthetic polynucleotide of FIGS. 3 and 6 will now be described in more detail.

The synthetic tropoelastin gene described here differs from the natural coding sequence(s) in a number of ways. The untranslated regions present in the tropoelastin cDNA sequence were disregarded in designing the synthetic gene, and the nucleotides encoding the signal peptide were removed. Restriction endonuclease recognition sites were incorporated at regular intervals into the gene by typically altering only the third base of the relevant codons, thereby maintaining the primary sequence of the gene product. The facility for silent alteration of the coding sequence was also exploited to change the codon bias of the tropoelastin gene to that commonly found in highly expressed *E. coli* genes. [Genetics Computer Group (GCG) package version 7-UNIX using Codon Frequency and Gen Run Data: ecohigh-cod]. Two additional stop codons were added to the 3'-end, and an ATG start codon comprising a novel NcoI site was appended to the 5'-end. Bam HI cloning sites were engineered at both ends of the synthetic sequence. Since the gene contains no internal methionine residues, treatment of the newly-synthesized gene product (expressed directly or as a fusion with another gene) with cyanogen bromide would liberate a protein with the same or similar sequence as one form of natural tropoelastin comprising 731 amino acids. Other forms of processing are envisaged, which may generate tropoelastin species of the same or different lengths.

Two stop codons were added in order to allow the possible use of the construct in suppressor hosts, and also to avoid any potential depletion of termination (release) factors for translation.

The inclusion of an ATG site is useful because: (1) it provides an appropriate restriction site for cloning, although this is a flexible property; (2) it provides a potential start codon for translation of an unfused synthetic gene; and (3) it introduces a methionine which can be cleaved by cyanogen bromide to release the tropoelastin species. However, another method of cleavage would not necessarily rely upon the availability of this methionine.

Fusion can provide a more stably expressed protein, and experience of other workers has suggested that unfused tropoelastin may be unstable (Indik et al., 1990). The fusion is typically to the carboxy terminus of the fusion protein (i.e. the N-terminus of the tropoelastin). Glutathione-S-transferase (Smith and Johnson, 1998) is an example of a suitable fusion protein.

A convergent approach was used in assembly and cloning of the synthetic human tropoelastin (SHEL) sequence. Groups of six, and in one case, eight, oligonucleotides were annealed and ligated together to generate eight synthetic blocks of approximately 260–300 bp, designated SHEL1–8. These blocks were cloned independently into pBluescript II SK+; the assembly and cloning scheme for SHEL1 is illustrated in FIG. 1. Following sequence confirmation, the blocks were excised from their parent plasmids and used to construct three clones, pSHEL α, β and γ, each containing approximately 700–800 bp of the synthetic gene. The final step towards assembly of the complete SHEL gene involved ligation of the inserts from each of these three intermediary clones into pBluescript II SK$^+$ to produce pSHEL. The cloning scheme is illustrated in FIG. 2.

The tropoelastin or variant produced as an expression product from vectors such as pSHEL can be chemically cross-linked to form an elastin product.

Three available procedures are:

1. chemical oxidation of lysine side chains which are conductive to cross-linking [eg ruthenium tetroxide-mediated oxidation, via the amide (Yoshifuji S; Tanaka K; and Nitto Y (1987) Chem. Pharm Bull 35 2994–3000) and quinone-mediated oxidation];
2. homobifunctional chemical cross-linking agents, such as dithiobis(succinimidylpropionate), dimethyl adipimidate and dimethyl pimelimidate. There are many other amine-reactive cross-linking agents which could be used as alternatives; and
3. cross-linking via lysine and glutamic acid side chains as taught by Rapaka et al (1983).

The tropoelastins or variants of the invention may also be enzymatically cross-linked to form an elastin or elastin-like product. Enzymatic methods include lysyl oxidase-mediated oxidation of the tropoelastin or variant via modification of peptidyl lysine [Beddell-Hogan et al (1993)]. Oxidised lysines participate in the generation of cross-linkages between and within tropoelastin molecules. Other modification enzymes can be used forming cross-links via lysine or other residues.

Cross-linking can also be achieved by gamma irradiation using, for instance, techniques adapted from Urry et al (1986).

Tropoelastins or variants of the invention cross-linked to form elastin or elastin-like products are also within the scope of the invention.

The half-lives of the products in free solution will determine the suitability of a particular agent for a particular application.

For example, the hydrolytic breakdown of the cross-linked material will be useful in applications, such as surgical applications, where the gradual loss of material over time is intended.

BRIEF DESCRIPTION OF THE DRAWINGS

The present invention is further described with reference to the accompanying drawings in which:

FIGS. 3 (1) to 3 (5) shows over 5 drawing sheets the full nucleotide sequence (SEQ ID NO: 1) and corresponding amino acid sequence (SEQ ID NO:2) for the synthetic human tropoelastin (SHEL). Coding (+) strand of the sHEL gene construct is shown on the upper (numbered) sequence line. Synthetic complementary (−) strand sequence is shown immediately beneath it. The amino acid sequence of the synthetic gene product is indicated below the nucleotide sequence.

FIGS. 4 (1) to 4 (2) shows over 2 drawings sheets the sequences for the oligonucleotides (SEQ ID NOS: 3 to 27) used to construct the synthetic human tropoelastin (SHEL) sequence: (+) − strand oligonucleotides.

FIGS. 5 (1) to 5 (2) shows over 2 drawing sheets the sequences for the oligonucleotides (SEQ ID NOS: 28 to 52) used to construct the synthetic human tropoelastin (SHEL) sequence: (−)− strand oligonucleotides.

FIGS. 6 (1) to 6 (4) shows over 4 drawing sheets the differences in nucleotide sequence between SHEL (SEQ ID NO: 1) and a cDNA form of the coding region of the human tropoelastin gene (SEQ ID NO: 53). The coding (+)− strand of the synthetic (SHEL) sequence is shown on the top (numbered line). The cDNA sequence is indicated below it, showing only those nucleotides which differ from the synthetic sequence.

——△—— Net data (%)

----○---- Expected (%)

FIGS. 9 (1) to 9 (2) over 2 drawing sheets shows the sequence (SEQ ID NO: 54) of the plasmid vector pND211.

Figure 10:
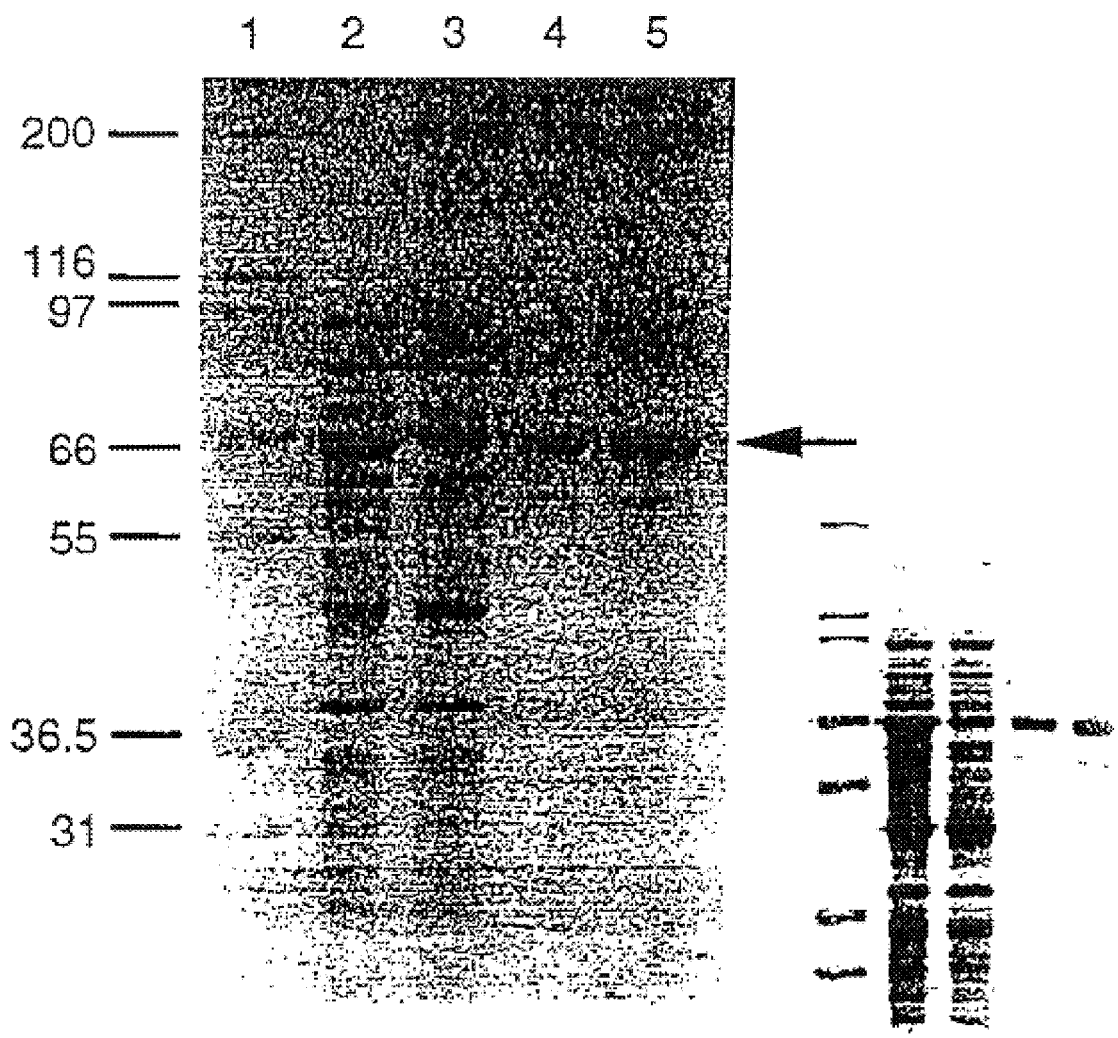

FIG. 10 shows the results of SDS-PAGE analysis of tropoelastin expression from pSHELF.

Lane 1: standards; Lane 2: induced; Lane 3: uninduced: Lane 4; alcohol-purified sample; Lane 5: additional lane of alcohol purified sample.

Figure 11:
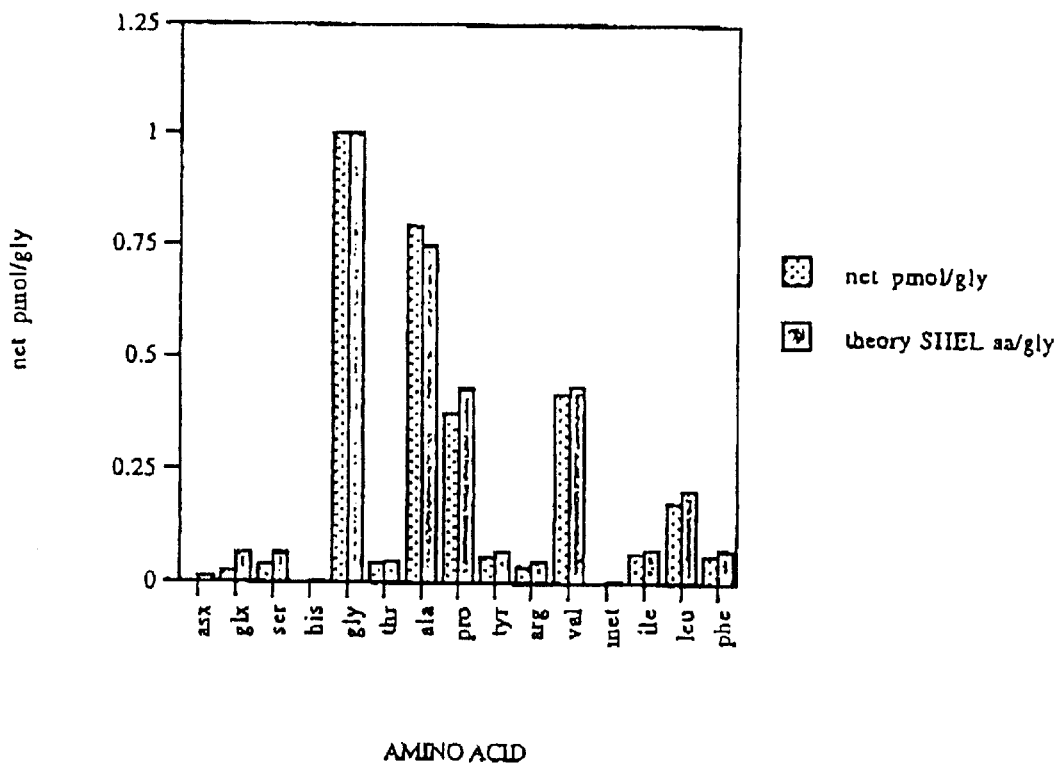

FIG. 11 shows the correlation between predicted and observed amino acid content for tropoelastin expressed from pSHELF.

BEST METHOD OF PERFORMING THE INVENTION

The recombinant and synthetic techniques used are standard techniques which are described in standard texts such as Sambrook et al (1989).

Purification of the expression products is also performed using standard techniques, with the actual sequence of steps in each instance being governed by the host/expression product combination.

The pharmaceutical and veterinary compositions are formulated in accordance with standard techniques.

The amount of expression product that may be combined with carrier to produce a single dosage form will vary depending upon the condition being treated, the host to be treated and the particular mode of administration.

It will be understood, also, that the specific dose level for any particular host will depend upon a variety of factors including the activity of the expression product employed, the age, body weight, general health, sex, diet of the patient, time of administration, route of administration, rate of excretion, drug combination, etc.

The compositions may be administered parenterally in dosage unit formulations containing conventional, non-toxic, pharmaceutically and/or veterinarally acceptable carriers, diluents, adjuvants and/or excipients as desired.

Injectable preparations, for example, sterile injectable aqueous or oleagenous suspensions may be formulated according to the known art using suitable dispersing or wetting agents and suspending agents. The sterile injectable preparation may also be a sterile injectable solution or suspension in a non-toxic parenterally acceptable diluent or solvent. Among the acceptable vehicles or solvents that may be employed are water, Ringer's solution, and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid and organic solvents find use in the preparation of injectables.

Routes of administration, dosages to be administered as well as frequency of administration are all factors which can be optimised using ordinary skill in the art.

In addition, the expression products may be prepared as topical preparations for instance as anti-wrinkle and hand lotions using standard techniques for the preparation of such formulations. They may be prepared in aerosol form for, for instance, administration to a patient's lungs, or in the form of surgical implants, foods or industrial products by standard techniques.

The tropoelastins can be cross-linked either chemically, enzymatically or by irradiation to form elastin products for use in applications such as pharmaceutical applications, surgical, veterinary and medical applications, cosmetic applications, and in industrial uses. Tropoelastin coacervates can be used to formulate slow release compositions of active ingredients or to form protective coatings for active ingredients using standard formulation techniques.

Materials and Methods

Materials

Restriction enzymes, T4 polynucleotide kinase and T4 DNA ligase were obtained from Boehringer Mannheim, Progen Industries or New England Biolabs. Gelase® was obtained from Epicentre Technologies. Reagents for solid-phase oligodeoxynucleotide synthesis were obtained from Applied Biosystems (ABI). Low melting temperature (LMT) agarose was obtained from Progen or FMC and α-$^{35}$S-dAPT was obtained from Amersham International. Plasmid vectors pBluescript II SK$^+$ and pGEX-2T were obtained from Stratagene and Medos Co Pty Ltd respectively. pET3d was obtained from F. W. Studier at Brookhaven National Laboratory, NY, U.S.A. E. coli strains HMS174 and BL21 (DE3) are described in Studier et al (1990).

Oligodeoxynucleotide Synthesis and Purification

Oligonucleotides were synthesized on 40 nmol-scale polystyrene-support columns on an Applied Biosystems 381A or 394 DNA synthesis machine. Standard ABI protocols were employed for synthesis, including chemical 5'-phosphorylation where appropriate. Detritylation was performed automatically, and cleavage from the solid support effected manually (381A) or automatically (394) according to the synthesizer used. Base protecting groups were removed by heating the ammoniacal oligonucleotide solution at 55–60° C. overnight. Deprotected oligonucleotides were lyophilized, dissolved in 400 μl TE buffer and ethanol precipitated prior to resuspension in 100 μl 50% deionized formamide in TE.

All oligonucleotides used in construction of the sHEL gene were purified by denaturing PAGE before use. 160 mm×100 mm×1.5 mm polyacrylamide gels containing 7M urea were used for this purpose. Short oligonucleotides (<40-mers) were purified on 20% gels whilst long oligonucleotides (>85-mers) were purified on gels containing 8–10% acrylamide (acrylamide:bisacrylamide 19:1). Samples were heated to 75° C. for 3 min before loading. Tracking dye (0.05% bromophenol blue, 0.05% xylene cyanole FF in deionized formamide) was loaded into an adjacent lane. Electrophoresis was conducted at constant power (17 W) until the bromophenol blue marker was within 1 cm of the base of the gel. The apparatus was disassembled and the gel wrapped in cling film. Product bands were visualized by UV-shadowing over a fluorescent TLC plate. Excised gel fragments containing purified oligonucleotides were transferred to microcentrifuge tubes, crushed and soaked overnight at 60° C. in 500 μl elution buffer (0.3M sodium acetate pH7.0). A second extraction was performed with 400 μl elution buffer, for 3–4 h at 60° C. and the supernatant combined with that of the first extraction. The total volume of the oligonucleotide-containing solution was reduced to approximately 400 μl by butan-1-ol extraction and DNA precipitated by addition of 1 ml ethanol. Purified oligonucleotide was pelleted by centrifugation, redissolved in 20 μl TE buffer and quantified by spectrophotometry. The final yield of purified oligonucleotide obtained in this manner was typically 10–30 μg.

Construction of Synthetic Gene 'Blocks' (sHEL1–8)

Complementary oligonucleotides (30 pmol each, approx 1 μl for 95-mers) were annealed in 10 μl buffer containing 50 mM Tris·HCl pH7.5, 10 mM MgCl$_2$. The mixture was overlayed with 12 μl paraffin oil, heated to 95° C. and cooled slowly to 16° C. (16 h) in a microprocessor-controlled heating block (Perkin Elmer Cetus Thermal Cycler). Annealed samples were transferred to clean microcentrifuge tubes and a small aliquot (1 μl) withdrawn for analysis by agarose gel electrophoresis (2% LTM gel, TBE running buffer). For each block comprising three complementary oligonucleotide pairs, four separate ligation reactions were set up. Each contained 50 mM Tris·HCl pH7.5, 10 mM MgCl$_2$, 1 mM ATP, 3 mM DTT, 3 μl each of the appropriate annealed samples, 0.5 μl (0.5 U) T4 DNA ligase and Milli-Q water to a total volume of 10 μl. All components except the ATP, DTT and T4 ligase were mixed and heated to 55° C. for 5 min to denature cohesive termini and cooled to room temperature before addition of the remaining components. Ligation reactions were incubated overnight at 16° C. and analysed on 2% LMT agarose gels, with TBE as running buffer. Ligated blocks were purified by preparative agarose gel electrophoresis using 2% LMT agarose gels with TAE running buffer. Product bands were identified under long-wave UV illumination with reference to known DNA size standards (pBluescript II SK$^+$ digested with Hae III) and excised in the minimum possible volume of gel. DNA was recovered from LMT agarose fragments using Gelase® in accordance with the manufacturer's instructions ("fast" protocol). Purity and yield of recovered sHEL blocks was assessed by analytical agarose electrophoresis alongside known DNA size standards. Block 8 was created by a slightly different strategy. The first 3 oligonucleotide pairs (numbers 22, 23, 24, 47, 48 and 49) were assembled and purified as described for blocks 1 to 7, after which the remaining oligonucleotide pair (numbers 25 and 50) was ligated under conditions described above. The full length block 8 was purified as described for blocks 1 to 7.

The oligonucleotides used for preparing each of the blocks shown in FIGS. 4 (1) to 4 (2) and 5 (1) to 5 (2) were assembled as follows:

| Block | +strand oligonucleotides | Seq ID. | −strand oligonucleotides | Seq ID |
|---|---|---|---|---|
| 1 | 1, 2, 3 | 3–5 | 26, 27, 28 | 28–30 |
| 2 | 4, 5, 6 | 6–8 | 29, 30, 31 | 31–33 |
| 3 | 7, 8, 9 | 9–11 | 32, 33, 34 | 34–36 |
| 4 | 10, 11, 12 | 12–14 | 35, 36, 37 | 37–39 |
| 5 | 13, 14, 15 | 15–17 | 38, 39, 40 | 40–42 |
| 6 | 16, 17, 18 | 18–20 | 41, 42, 43 | 43–45 |
| 7 | 19, 20, 21 | 21–23 | 44, 45, 46 | 46–48 |
| 8 | 22, 23, 24, 25 | 24–27 | 47, 48, 49, 50 | 49–52 |

Blocks 1–8

Cloning pBluescript II SK+ DNA was digested with appropriate restriction enzymes and purified at each stage by preparative gel electrophoresis (1% agarose, TAE buffer). Plasmid DNA was isolated from agarose using a proprietary DNA purification matrix (Prep-A-Gene, Bio-Rad). Approximately 100 ng (ca. 0.05 pmol) of purified plasmid fragment was added to 50 ng (ca. 0.3 pmol) synthetic block in 17 $\mu$l buffer containing 50 mM Tris·HCl pH7.5, 10 mM MgCl$_2$ and the mixture heated at 55° C. for 5 min to denature cohesive termini. Upon cooling to room temperature, 2 $\mu$l 10 mM ATP, 30 mM DTT and 1 $\mu$l T4 DNA ligase (1 U) were added and the reaction incubated overnight at 16° C. TE buffer was added to a final volume of 50 $\mu$l and DNA precipitated with 150 $\mu$l ethanol. Pelleted DNA was dissolved in 10 $\mu$l TE and 1 $\mu$l of the solution used to transform *E. coli* XL1-Blue (Bullock et al, 1987) by electroporation. Transformants were selected on LB plates containing ampicillin (50 $\mu$gml$^{-1}$), IPTG (0.1 mM) and X-gal (80 $\mu$gml$^{-1}$). Clones were screened following DNA extraction by restriction mapping and DNA sequence analysis.

The restriction enzymes used to digest pBluescript II SKF+ for the cloning of each of these blocks were as follows:

| Block | pBluescript II SK+ digested with: |
|---|---|
| 1 | KpnI, BamHI |
| 2 | KpnI, HindIII |
| 3 | HindII, NotI |
| 4 | NotI, SacI |
| 5 | SpeI, SacI |
| 6 | KpnI, SpeI |
| 7 | KpnI, PstI |
| 8 | BamHI, PstI |

Construction of pSHELα,β and γ

Figure 1:
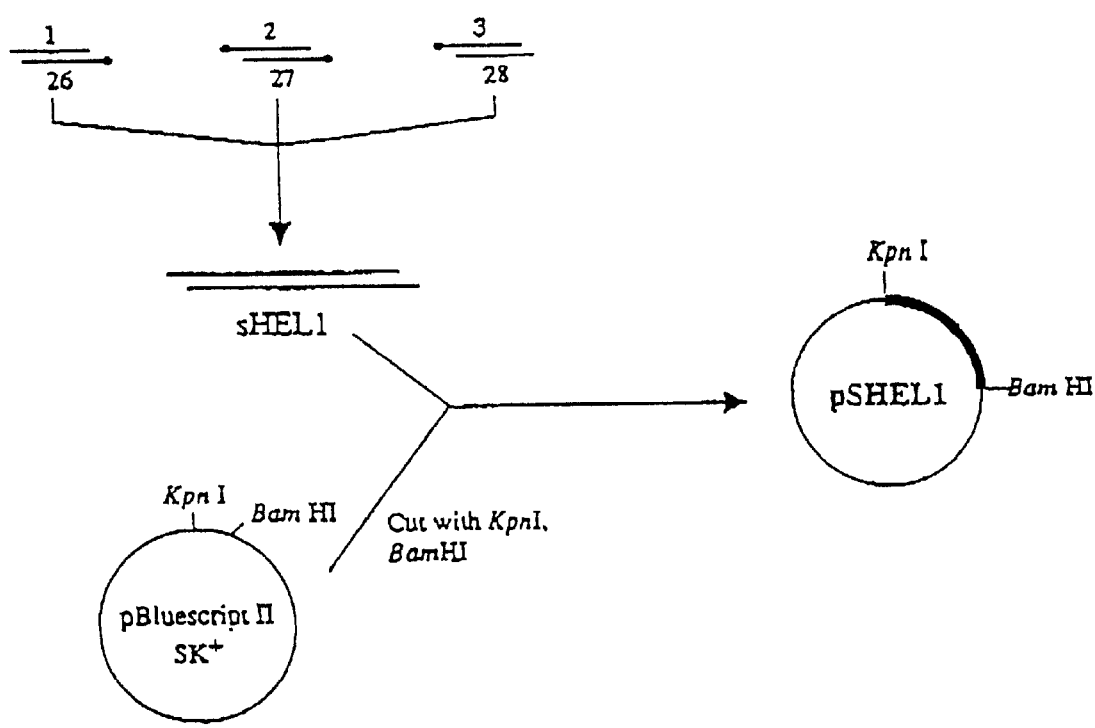
FIG. 1 shows the scheme for construction and cloning of SHEL1, one of the eight intermediary subassemblies used to generate the SHEL sequence. A similar approach was adopted for each of the remaining blocks (sHEL 2–8). See materials and methods section for details. 5'-phosphorylated oligonucleotides are indicated with a black dot (•).
Figure 2:
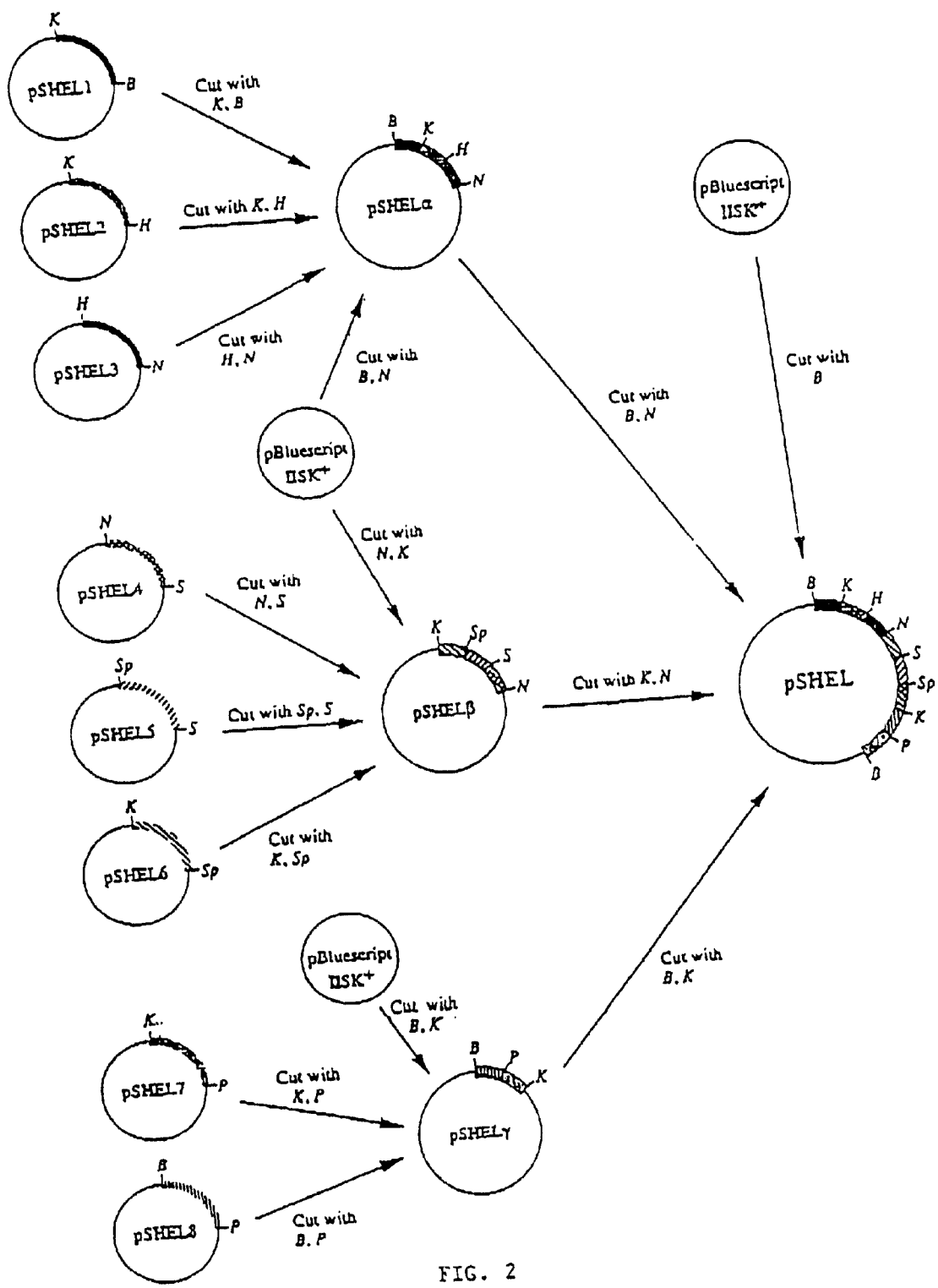
FIG. 2 shows the cloning scheme for the synthetic human tropoelastin (SHEL)—Abbreviations: B,Bam HI; H,HindIII; K,KphI; N,NotI; P,PstI; S,SacI; Sp,SpeI.

Two (pSHELγ) or three (pSHELα,β) blocks were ligated into pBluescript II SK+ in a single reaction. Each block was excised from the appropriate pBluescript II SK+-derived plasmid and purified by preparative agarose gel electrophoresis. 25 ng (ca. 0.15 pmol) of each synthetic block (eg. blocks 1–3 in the case of pSHELα) and 150 ng (ca. 0.075 pmol) of the appropriate pBluescript II SK+ fragment were ligated in a total reaction volume of 20 $\mu$l under conditions similar to those used to assemble the individual blocks. Transformants were screened by restriction analysis. The digestion schemes are illustrated in FIG. 2.

Final Assembly of the SHEL Gene

The three gene subassemblies pSHELα,β and γ were excised from their parent plasmids by treatment with the appropriate restriction enzymes (see cloning scheme) and purified by agarose gel electrophoresis. 100 ng of pBluescript II SK+ DNA linearised with BamH1 and treated with calf alkaline phosphatase. This and 50 ng (ca. 0.10 pmol) of each subassembly were ligated at 16° C. for 1 hour using the DNA Ligation Kit (Amersham International plc) according to the supplied protocol. Transformants were selected on LB-ampicillin plates containing IPTG and X-gal, and analysed by restriction mapping. The two orientations of the SHEL gene in pBluescript were designated pSHELA and pSHELB.

Expression

The full length SHEL gene was excised from pSHELB with BamHI and purified by gel electrophoresis. 200 ng of the purified fragment was ligated with 100 ng pGEX-2T linearized with BamHI and treated with calf alkaline phosphatase using the DNA Ligation Kit (Amersham International plc) according to the supplied protocol. Transformants were selected on LB-ampicillin plates and screened by restriction mapping. The SHEL gene cloned into pGEX-2T was designated pSHELC.

Figure 7:
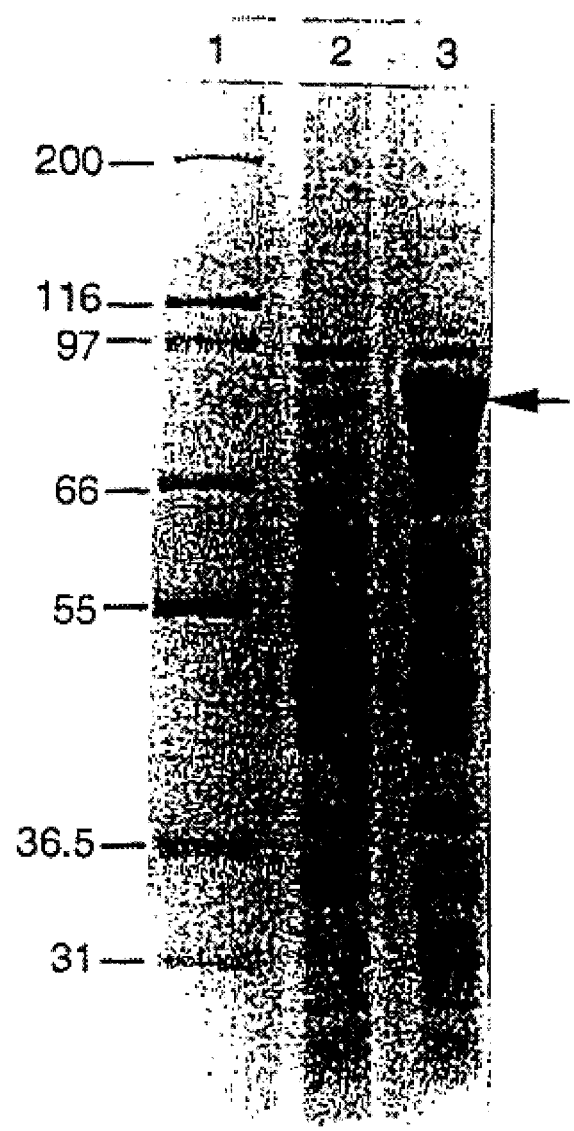
FIG. 7 shows the results of SDS-PAGE analysis of tropoelastin fusion protein expression from pSHELC. Lane 1: standards; Lane 2: non-induced; Lane 3: induced. The arrow points to the overexpressed fusion protein.
Figure 8:
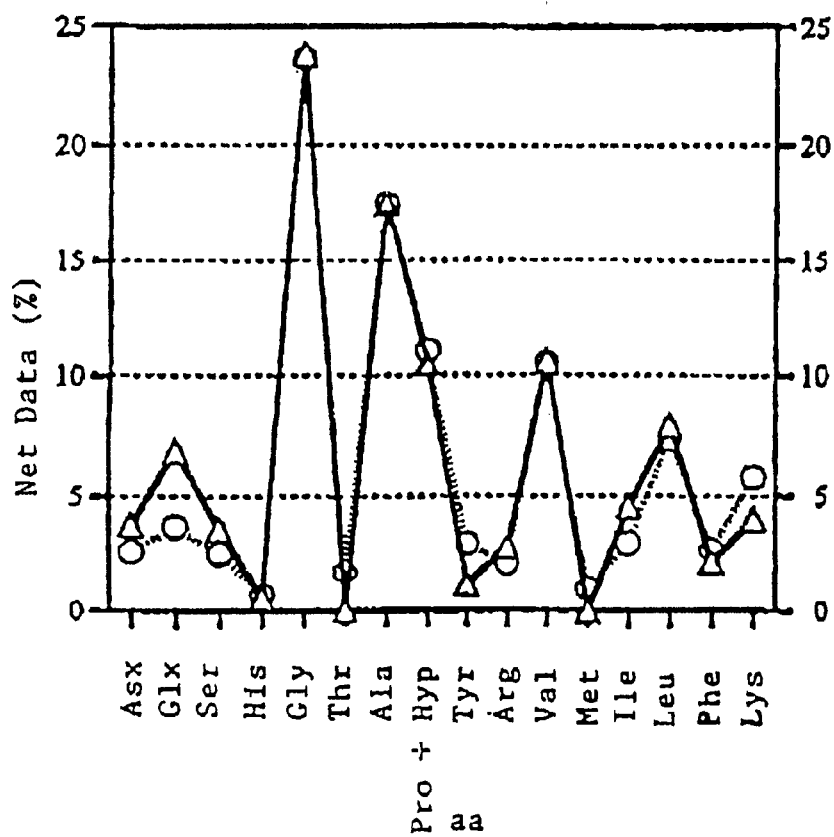
FIG. 8 shows the correlation between predicted and observed amino acid content for the fusion protein expressed from pSHELC.

Small scale expression of pSHELC was achieved by growing 5 ml cultures of *E. coli* DH5α containing pSHELC in LB with 50 $\mu$g/ml ampicillin and 0.2% glucose at 37° C. overnight. 250 $\mu$l was subinoculated into 5 ml 2 TY and grown to an A$_{600}$ of approximately 0.8 before being induced with 1 mM IPTG. Cultures were grown for a further 3 hours before harvesting. For the analysis of total cell protein 1 ml culture was harvested by centrifugation and resuspended in 200 $\mu$l SDS-PAGE loading buffer. 20 $\mu$l samples were boiled for 5 minutes before being analyzed on an 8% SDS-PAGE gel. For the analysis of soluble and insoluble protein, the bacterial pellet from 3 ml culture was resuspended in 500 $\mu$l lysis buffer (50 mM Tris-HCl pH 8, 1 mM EDTA, 100 mM NaCl) and lysed by the addition of 1 mg/ml lysozyme at 4° C. for 30 minutes followed by 1% triton X-100 for 20 minutes. After the addition of 0.1 mg/ml DNase samples were sonicated. The samples were centrifuged for 15 minutes in a microfuge and the pellet resuspended in an identical volume of lysis buffer as supernatant. 20 $\mu$l samples of supernatant and resuspended pellet were boiled for 5 minutes and analysed by 8% SDS-PAGE. (FIG. 7). The calculated size of the protein from SDS-PAGE was 86 kD which is in close agreement with the predicted size of 90 kD. The protein was over 75% soluble under the conditions used. Total amino acid content of the fusion protein was determined and the results show a high correlation with the predicted values (FIG. 8). The total level of expression was determined using SDS-PAGE and scanning densitometry and was found to be in excess of 100 mg/l.

After purification of GST away from SHEL a yield of up to 70 mg/l could theoretically be obtained.

Even allowing for losses during purification this is a highly significant improvement over 4 mg/l obtained with cDNA clones (Indik et al 1990). Optimising codon preference has therefore increased the potential yield of tropoelastin fifteenfold.

Alternatively, the SHEL gene was excised from pSHELB with both NcoI and BamHI and purified as above. 100 ng of the purified fragment was ligated to 50 ng pET3d, previously digested with NcoI and BamHI, using the Amersham DNA Ligation Kit to give pSHELF. pSHELF was used to transform *E. coli* HMS174. After confirmation, pSHELF was extracted from HMS174 and used to transform BL21. In both cases, transformants were selected on LB-ampicillin plates and screened by restriction mapping.

For pSHELF expression, 5 ml LB containing 50 $\mu$gml$^{-1}$ ampicilin was inoculated with a single colony of *E. coli*

BL21 (DE3) containing pSHELF and incubated overnight at 37° C. with shaking. 0.25 ml of this culture was used to inoculate 5 ml fresh LB containing 50 $\mu$gml$^{-1}$ ampicillin and grown to early log phase (A$_{600}$=0.8 approx). IPTG was added to a final concentration of 0.4 mM and growth continued for a further 3 h. Total cellular protein was analysed as for pSHELC. Cell lysates were prepared by resuspension of the cell pellet in 9 volumes lysis buffer and incubation at 4° C. for 30 min with 1 mgml$^{-1}$ lysozyme. PMSF was added to 0.5 mM before the mixture was twice frozen in liquid nitrogen and thawed at 37° C. DNase was added to a concentraton of 0.1 mgml$^{-1}$ with 10 mM MgCl$_2$ and incubated for 20 min at room temperature or until the solution was no longer viscous. Insoluble material was removed by centrifugation at 20 000 rpm for 25 min.

The soluble cell lysate from 125 ml culture was extracted by use of a modified version of a technique previously described for tropoelastin isolation (Sandberg et al., 1971). 1.5 volumes of n-propanol was added to the lysate in five aliquots over 2 hours followed by 2.5 volumes of n-butanol. All additions were performed at 4° C. with constant stirring and the mixture was allowed to extract overnight. The precipitated protein was removed by centrifugation for 15 min at 10 000 rpm. The soluble alcohol fraction was frozen and dried via a vacuum pump coupled to a liquid nitrogen trap. The residue was dissolved in 3.5 ml 25 mM HEPES pH 8.0 and dialyzed against 1 l of the same buffer for 2 hours, changed to fresh buffer and dialyzed overnight. The butanol precipitated protein was dissolved in an identical volume SDS-PAGE loading buffer and both fractions were analyzed by SDS-PAGE.

The butanol-extracted protein containing SHEL was further purified by size fractionation using a Superose 12 column and FPLC (Pharmacia). Protein was eluted using 25 mM HEPES, pH 8.0. at a flow rate of 0.5 mlmin$^{-1}$.

Protein concentration was estimated using a Bradford assay (Ausubel et al., 1989).

Scanning densitometry of gels was performed on a Molecular Dynamics Personal Densitometer and analyzed using ImageQuant software.

From SDS-PAGE the directly-expressed SHEL was calculated as being 64 kDa (FIG. 10) which is as predicted. Total amino acid content was determined and was found to be in close agreement with predictions further confirming the nature of the overexpressed protein. The analysis (FIG. 11) performed omits lysine residues.

Scanning densitometry of gels was used to estimate the relative level of overexpression. SHEL was expressed at a level of approximately 17% total cell protein in the range 20–200 kDa. This represents a substantial level of overexpression and confirms the value of codon manipulation for high level expression.

As a result of the high levels of expression large quantities of tropoelastin were obtained which can be used for further studies. The directly expressed SHEL protein appeared stable and the rapid degradation seen previously with cDNA expression (Indik et al., 1990) was not observed. Therefore, the purification of the free polypeptide was pursued in preference to fusion protein. A technique utilizing tropoelastin's high solubility in short-chained alcohols has been used previously in the extraction and purification of tropoelastin from tissues (Sandberg et al., 1971). This method was modified for use with soluble cell lysates and found to be very effective. SHEL was selectively extracted into the alcohols while the majority of contaminating protein was precipitated and removed (FIG. 10). The yield of SHEL after this step was high (greater than 90%) despite some loss (less than 10%) by precipitation. The resulting SHEL was of high purity as judged by SDS-PAGE after Coomassie staining (estimated by eye to be of the order greater than 80%). A gel filtration step was used to remove the contaminating protein after which the SHEL was of sufficient purity for further characterization.

Cross-linking of Tropoelastin

Tropoelastin obtained from PSHELF (0.3 mg/ml) was chemically cross-linked using 1 mM dithiobis (succinimidylpropionate) at 37° C. to generate an insoluble material with elastin-like properties. Cross-linking was demonstrated by boiling in the presence of sodium dodecyl sulphate (SDS) followed by SDS-polyacrylamide gel electrophoresis. Cross-linked material did not enter the gel under conditions designed to allow entry of uncross-linked material.

Industrial Applications

Cosmetic Applications

Recombinant tropoelastin is similar or identical to material found in skin and other tissues and involves no animal death in order to make it. It adds to our own skin's supply of tropoelastin. Recombinant tropoelastins can be used in humans or animals.

Additionally, methods such as liposome technology may be considered to deliver substances deep within the skin.

Another significant area of use for tropoelastin is in minimising scar formation. The availability of large amounts of recombinant tropoelastin means that it should be possible to test whether the scarring obtained from severe cuts and burns can be minimised by regular application of tropoelastin to the affected area. Increased skin elasticity will counter the rigid effects of collagen buildup associated with scar formation, both in human and veterinary applications.

Surgical and Veterinary Applications

The tropoelastins and variants of this invention may be used in the repair and treatment of elastic and non-elastic tissues. They may also be used as food supplements.

REFERENCES

1. Bressan, G. M., Argos, P. and Stanley, K. K. (1987) *Biochemistry* 26, 1497–1503.
2. Fazio, M. J., Olsen, E. A., Kauh, E. A., Baldwin, C. T., Indik, Z., Ornstein-Goldstein, N., Yeh, H., Rosenbloom, J. and Uitto, J. (1988) *J. Invest. Dermatol.* 91, 458–464.
3. Indik, Z., Yeh, H., Ornstein-Goldstein, N., Sheppard, P., Anderson, N., Rosenbloom, J. C., Peltonen, L. and Rosenbloom, J. (1987) *Proc. Natl. Acad. Sci. USA* 84, 5680–5684.
4. Indik, Z., Abrams, W. R., Kucich, U., Gibson, C. W., Mecham, R. P. and Rosenbloom, J. (1990) *Arch. Biochem. Biophys.* 280, 80–86.
5. Oliver, L., Luvalle, P. A., Davidson, J. M., Rosenbloom, J., Mathew, C. G., Bester, A. J. and Boyd, C. D. (1987) *Collagen Rel. Res.* 7, 77–89.
6. Alting-Mees, M. A. and Short, J. M. (1989) *Nucl. Acids Res.* 17, 9494—9494.
7. Bullock, W. O., Fernandez, J. M. and Short, J. M. (1987) *BioTechniques* 5, 376–379.
8. Gough, J. and Murray, N. (1983) *J.Mol.Biol.* 166, 1–19.
9. Short, J. M., Fernandez, J. M., Sorge, J. A. and Huse, W. D. (1988) *Nucl. Acids Res.* 16, 7583–7600.
10. Smith, D. B. and Johnson, K. S. (1988) *Gene* 67, 31–40.
11. Studier, F. W., Rosenberg, A. H., Dunn, J. J. and Dubendorff, J. W. (1990) *Methods Enzymol.* 185, 60–89.
12. Lipman and Pearce (1985) *Science* 227, 1435.
13. Heim, R. A., Pierce, R. A., Deak, S. B., Riley, D. J., Boyd, C. D. and Stolle, C. A., (1991) *Matrix* II 359–366.

14. Raju, K., and Anwar, R. A., (1987) J. Biol. Chem. 262 5755–5762.
15. Yeh, H., Ornstein-Goldstein N., Indik, Z., Sheppard, P., Anderson, N., Rosenbloom, J. C., Cicila, G., Yoon, K. and Rosenbloon, J., (1987) Coll. Relat. Res. 7 235–247.
16. Zhang, S., Zubay, G. and Goldman, E., (1991) Gene 105 61–72.
17. Newgard, C. B., Nakano, K., Hwang, P. K., and Fletterick, R. J., (1986) PNAS (USA) 83:8132–8136.
18. Murray, E. E., Lotzer, J., Eberle, M. (1989) Nucleic Acids Res. 17 477–498.
19. Sambrook, J., Fritsch E. F., and Maniatis, T., (1989) Molecular cloning: a laboratory manual, second edition, Cold Spring Harbor Laboratory Press, Cold Spring Harbor, N.Y.
20. Yoshifuji S; Tanaka K; and Nitto Y (1987) Chem Pharm Bull 35 2994–3000
21. Urry D. W., Haynes B and Harris R D (1986) Biochem Biophys Res. Comm 141 749–55
22. Rapaka R S; Okamoto K., Long M. M. and Urry D. W. (1983) International Journal of Peptide and Protein Research 21 352–363.
23. Bedell-Hogan D., Trackman P., Abrams W. Rosenbloom J. and Kagan H (1993) J Biol Chem 268 10345–10350.
24. Sandberg L. B., Zeikus R. D. and Coltrain I. M. (1971) Biochem Biophys Acta 236 542–545.
25. Ausubel F. M., Brent R., Kingston R. E., Moore D. D., Seidman J. G., Smith J. A. and Struhl K. (1987) Current protocols in molecular biology. Greene Publishing Associates and Wiley Interscience, U.S.A.

What is claimed is:

1. A synthetic polynucleotide encoding tropoelastin said polynucleotide comprising the sequence depicted in FIG. 3(1) to 3(5) (SEQ ID NO:1).

2. A vector comprising the synthetic polynucleotide according to claim 1 under the control of sequences which direct expression of said tropoelastin.

3. A host cell transformed with a vector comprising a synthetic polynucleotide according to claim 1, wherein said synthetic polynucleotide is heterologous to said host cell.

4. A synthetic polynucleotide which consists of the sequence shown in SEQ ID NO:1.

5. A vector comprising a synthetic polynucleotide according to claim 1 or 4.

6. The vector according to claim 5, wherein the vector is pBluescript II SK+, pBR322 or pTrc99A.

7. The vector according to claim 6, wherein the vector is pSHELA or pSHELB.

8. The vector according to claim 5 wherein the vector further comprises a nucleic acid molecule which is capable of encoding a peptide which is linked by a peptide bond to a peptide encoded by the synthetic polynucleotide.

9. The vector according to claim 8, wherein the peptide encoded by the nucleic acid molecule is glutathionine-S-transferase.

10. The vector according to claim 9, wherein the vector is pGEX-2T.

11. The vector according to claim 10, wherein the vector is pSHELC.

12. The vector according to claim 5, wherein the vector is pET3d.

13. The vector according to claim 12, wherein the vector is pSHELF.

14. A cell containing a vector comprising a synthetic polynucleotide according to claim 1 or 4.

15. The cell according to claim 14, wherein the cell is *E. coli*.

16. The cell according to claim 15, wherein the *E. coli* is selected from the group of *E. coli* consisting of NM522, DH5α, XL1-Blue, BL21 and HMS174.

17. The cell according to claim 14, wherein the vector is pBluescript II SK+, pBR322 or pTrc99A.

18. The cell according to claim 17, wherein the vector is pSHELA or pSHELB.

19. The cell according to claim 14, wherein the vector further comprises a nucleic acid molecule which is capable of encoding a peptide which is linked by a peptide bond to a peptide encoded by the synthetic polynucleotide.

20. The cell according to claim 19, wherein the peptide encoded by the nucleic acid molecule is glutathionine-S-transferase.

21. The cell according to claim 19, wherein the vector is pGEX-2T.

22. The cell according to claim 21, wherein the vector is pSHELC.

23. A plasmid selected from the group consisting of pSHELA, pSHELB, pSHELC and pSHELF, wherein the synthetic human tropoelastin gene in pSHELA, pSHELB and pSHELC comprises SEQ ID NO:1, and wherein the synthetic human tropoelastin gene in pSHELF, comprises nucleotides 4 to 2210 of SEQ ID NO:1.

24. A host cell transformed with a plasmid according to claim 23.

* * * * *